(12) United States Patent
Brigido

(10) Patent No.: US 9,226,783 B2
(45) Date of Patent: *Jan. 5, 2016

(54) ANKLE ARTHRODESIS NAIL AND OUTRIGGER ASSEMBLY

(71) Applicant: Icon Orthopaedic Concepts, LLC, Bethlehem, PA (US)

(72) Inventor: Stephen A. Brigido, Bethlehem, PA (US)

(73) Assignee: Icon Orthopaedic Concepts, LLC, Bethlehem, PA (US)

( * ) Notice: Subject to any disclaimer, the term of this patent is extended or adjusted under 35 U.S.C. 154(b) by 129 days.

This patent is subject to a terminal disclaimer.

(21) Appl. No.: 13/858,461

(22) Filed: Apr. 8, 2013

(65) Prior Publication Data

US 2013/0296862 A1 Nov. 7, 2013

Related U.S. Application Data

(63) Continuation of application No. 12/938,311, filed on Nov. 2, 2010, now Pat. No. 8,414,584, which is a continuation-in-part of application No. 12/500,473, filed on Jul. 9, 2009, now Pat. No. 8,328,807.

(60) Provisional application No. 61/079,130, filed on Jul. 9, 2008, provisional application No. 61/079,132, filed on Jul. 9, 2008.

(51) Int. Cl.
*A61B 17/72* (2006.01)
*A61B 17/17* (2006.01)

(52) U.S. Cl.
CPC ......... *A61B 17/7225* (2013.01); *A61B 17/1725* (2013.01); *A61B 17/7233* (2013.01); *A61B 17/7291* (2013.01); *A61B 2017/1775* (2013.01)

(58) Field of Classification Search
CPC ............ A61B 17/1725; A61B 17/7225; A61B 2017/1775; A61B 17/7291; A61B 17/7233
USPC ........... 606/62–64, 86 R, 87–89, 96–98, 280, 606/281, 286, 300, 301
See application file for complete search history.

(56) References Cited

U.S. PATENT DOCUMENTS 3,946,728 A 3/1976 Bettex
3,979,779 A 9/1976 Zeibig et al.
(Continued)

FOREIGN PATENT DOCUMENTS

WO WO 9722301 6/1997
WO WO 2007133643 11/2007
WO WO 2008007378 1/2008

OTHER PUBLICATIONS

International Search Report for International Application No. PCT/US2009/050149, mailed Sep. 3, 2009, 1 page.
(Continued)

*Primary Examiner* — Pedro Philogene
(74) *Attorney, Agent, or Firm* — Sterne, Kessler, Goldstein & Fox P.L.L.C.

(57) ABSTRACT

An intramedullary fixation device having a distal section; a proximal section; a connecting member for adjustably securing the distal and proximal sections end to end along a longitudinal axis; means for securing the proximal section to a first bone; and means for securing the distal section to a least one different bone. The connecting member is rotated to provide compression across a bone arthrodesis site to be stabilized and fused. Also described is a method of utilizing the intramedullary fixation device with an outrigger assembly.

8 Claims, 14 Drawing Sheets

(56) References Cited

U.S. PATENT DOCUMENTS

| | | | |
|---|---|---|---|
| 4,010,494 A | 3/1977 | Sauer | |
| 4,011,603 A | 3/1977 | Steffee | |
| 4,157,715 A | 6/1979 | Westerhoff | |
| 4,158,895 A | 6/1979 | Frosch et al. | |
| 4,187,841 A | 2/1980 | Knutson | |
| 4,262,665 A | 4/1981 | Roalstad | |
| 4,281,649 A | 8/1981 | Derweduwen | |
| 2,895,124 A | 9/1981 | Zickel | |
| 4,313,434 A | 2/1982 | Segal | |
| 4,409,974 A | 10/1983 | Freedland | |
| 4,433,681 A | 2/1984 | Comparetto | |
| 4,456,005 A | 6/1984 | Lichty | |
| 4,522,202 A | 6/1985 | Otte | |
| 4,530,114 A | 7/1985 | Tepic | |
| 4,532,660 A | 8/1985 | Field | |
| 4,550,449 A | 11/1985 | Tunc | |
| 4,574,795 A | 3/1986 | Georges | |
| 4,629,463 A | 12/1986 | Grundei et al. | |
| 4,644,943 A | 2/1987 | Thompson | |
| 4,649,918 A | 3/1987 | Pegg et al. | |
| 4,677,973 A | 7/1987 | Slocum | |
| 4,706,367 A | 11/1987 | Garringer | |
| 4,711,234 A | 12/1987 | Vives et al. | |
| 4,756,307 A | 7/1988 | Crowninshield | |
| 4,781,591 A | 11/1988 | Allen | |
| 4,784,126 A | 11/1988 | Hourahane | |
| 4,784,127 A | 11/1988 | Mattheck et al. | |
| 4,792,336 A | 12/1988 | Hlavacek et al. | |
| 4,858,601 A * | 8/1989 | Glisson | 606/916 |
| 4,858,602 A | 8/1989 | Seidel et al. | |
| 4,858,603 A | 8/1989 | Clemow et al. | |
| 4,865,604 A | 9/1989 | Rogozinski | |
| 4,865,609 A | 9/1989 | Roche | |
| 4,875,475 A | 10/1989 | Comte | |
| 4,921,499 A | 5/1990 | Hoffman et al. | |
| 4,923,471 A | 5/1990 | Morgan | |
| 4,931,055 A | 6/1990 | Bumpus et al. | |
| 4,936,844 A | 6/1990 | Chandler et al. | |
| 4,938,768 A | 7/1990 | Wu | |
| 4,944,743 A | 7/1990 | Gotzen et al. | |
| 4,946,459 A | 8/1990 | Bradshaw | |
| 4,957,497 A | 9/1990 | Hoogland et al. | |
| 4,964,403 A | 10/1990 | Karas et al. | |
| 4,969,888 A | 11/1990 | Scholten et al. | |
| 4,976,737 A | 12/1990 | Leake | |
| 4,976,739 A | 12/1990 | Duthie, Jr. | |
| 4,983,745 A | 1/1991 | Muller et al. | |
| 4,998,936 A | 3/1991 | Mehdian | |
| 5,009,664 A | 4/1991 | Sievers | |
| 5,009,666 A | 4/1991 | Van Syckle et al. | |
| 5,013,313 A | 5/1991 | Surer | |
| 5,034,012 A | 7/1991 | Frigg | |
| 5,035,697 A | 7/1991 | Frigg | |
| 5,053,034 A | 10/1991 | Olerud | |
| 5,059,193 A | 10/1991 | Kuslich | |
| 5,067,956 A | 11/1991 | Buford, III et al. | |
| 5,084,049 A | 1/1992 | Asher et al. | |
| 5,085,660 A | 2/1992 | Lin | |
| 5,087,259 A | 2/1992 | Krenkel | |
| 5,092,866 A | 3/1992 | Breard et al. | |
| 5,092,893 A | 3/1992 | Smith | |
| 5,098,433 A | 3/1992 | Freedland | |
| 5,102,421 A | 4/1992 | Anspach, Jr. | |
| 5,108,397 A | 4/1992 | White | |
| 5,108,404 A | 4/1992 | Scholten et al. | |
| 5,108,443 A | 4/1992 | Branemark | |
| 5,108,449 A | 4/1992 | Gray | |
| 5,112,332 A | 5/1992 | Cozad et al. | |
| 5,112,333 A | 5/1992 | Fixel | |
| 5,116,334 A | 5/1992 | Cozad et al. | |
| 5,116,336 A | 5/1992 | Frigg | |
| 5,116,337 A | 5/1992 | Johnson | |
| 5,122,133 A | 6/1992 | Evans | |
| 5,122,141 A | 6/1992 | Simpson et al. | |
| 5,123,926 A | 6/1992 | Pisharodi | |
| 5,129,902 A | 7/1992 | Goble et al. | |
| 5,133,715 A | 7/1992 | Lenzo | |
| 5,133,716 A | 7/1992 | Plaza | |
| 5,133,718 A | 7/1992 | Mao | |
| 5,133,771 A | 7/1992 | Duncan et al. | |
| 5,139,497 A | 8/1992 | Tilghman et al. | |
| 5,141,520 A | 8/1992 | Goble et al. | |
| 5,147,359 A | 9/1992 | Cozad et al. | |
| 5,147,367 A | 9/1992 | Ellis | |
| 5,147,402 A | 9/1992 | Bohler et al. | |
| 5,152,794 A | 10/1992 | Davidson | |
| 5,154,718 A | 10/1992 | Cozad et al. | |
| 5,176,678 A | 1/1993 | Tsou | |
| 5,176,680 A | 1/1993 | Vignaud et al. | |
| 5,180,388 A | 1/1993 | DiCarlo | |
| 5,190,545 A | 3/1993 | Corsi et al. | |
| 5,190,546 A | 3/1993 | Jervis | |
| 5,192,281 A | 3/1993 | de la Caffiniere | |
| 5,192,327 A | 3/1993 | Brantigan | |
| 5,196,014 A | 3/1993 | Lin | |
| 5,201,733 A | 4/1993 | Etheredge, III | |
| 5,201,735 A | 4/1993 | Chapman | |
| 5,207,712 A | 5/1993 | Cohen | |
| 5,211,664 A | 5/1993 | Tepic et al. | |
| 5,234,430 A | 8/1993 | Huebner | |
| 5,242,443 A | 9/1993 | Kambin | |
| 5,242,444 A | 9/1993 | MacMillan | |
| 5,242,446 A | 9/1993 | Steffee et al. | |
| 5,246,441 A | 9/1993 | Ross et al. | |
| 5,246,458 A | 9/1993 | Graham | |
| 5,248,313 A | 9/1993 | Greene et al. | |
| 5,250,048 A | 10/1993 | Gundolf | |
| 5,254,118 A | 10/1993 | Mirkovic | |
| 5,257,994 A | 11/1993 | Lin | |
| 5,261,907 A | 11/1993 | Vignaud et al. | |
| 5,261,909 A | 11/1993 | Sutterlin et al. | |
| 5,263,954 A | 11/1993 | Schlapfer et al. | |
| 5,263,955 A * | 11/1993 | Baumgart et al. | 606/63 |
| 5,263,980 A | 11/1993 | Leibinger et al. | |
| 5,268,000 A | 12/1993 | Ottieri | |
| 5,282,802 A | 2/1994 | Mahony, III | |
| 5,282,862 A | 2/1994 | Baker et al. | |
| 5,303,718 A | 4/1994 | Krajicek | |
| 5,306,275 A | 4/1994 | Bryan | |
| 5,318,566 A | 6/1994 | Miller | |
| 5,324,291 A | 6/1994 | Ries et al. | |
| 5,324,292 A | 6/1994 | Meyers | |
| 5,330,472 A | 7/1994 | Metz-Stavenhagen | |
| 5,330,474 A | 7/1994 | Lin | |
| 5,330,476 A | 7/1994 | Hiot et al. | |
| 5,336,225 A | 8/1994 | Zang | |
| 5,342,361 A | 8/1994 | Yuan et al. | |
| 5,344,422 A | 9/1994 | Frigg | |
| 5,344,457 A | 9/1994 | Piliar et al. | |
| 5,346,492 A | 9/1994 | Morgan | |
| 5,348,026 A | 9/1994 | Davison | |
| 5,360,448 A | 11/1994 | Thramann | |
| 5,366,455 A | 11/1994 | Dove et al. | |
| 5,370,646 A | 12/1994 | Reese et al. | |
| 5,376,126 A | 12/1994 | Lin | |
| 5,382,248 A | 1/1995 | Jacobson et al. | |
| 5,387,217 A | 2/1995 | Sefcik et al. | |
| 5,397,328 A | 3/1995 | Behrens et al. | |
| 5,397,363 A | 3/1995 | Gelbard | |
| 5,413,602 A | 5/1995 | Metz-Stavenhagen | |
| 5,425,767 A | 6/1995 | Steininger et al. | |
| 5,425,776 A | 6/1995 | Cohen | |
| 5,429,638 A | 7/1995 | Muschler et al. | |
| 5,433,720 A | 7/1995 | Faccioli et al. | |
| 5,443,509 A | 8/1995 | Boucher et al. | |
| 5,449,359 A | 9/1995 | Groiso | |
| 5,454,811 A | 10/1995 | Huebner | |
| 5,458,600 A | 10/1995 | Stapert | |
| 5,458,608 A | 10/1995 | Wortrich | |
| 5,466,243 A | 11/1995 | Schmieding et al. | |
| 5,466,261 A | 11/1995 | Richelsoph | |
| 5,468,242 A | 11/1995 | Reisberg | |
| 5,476,462 A | 12/1995 | Allard et al. | |
| 5,480,400 A | 1/1996 | Berger | |

(56) References Cited

U.S. PATENT DOCUMENTS

| | | |
|---|---|---|
| 5,480,440 A | 1/1996 | Kambin |
| 5,487,741 A | 1/1996 | Maruyama et al. |
| 5,490,851 A | 2/1996 | Nenov et al. |
| 5,496,318 A | 3/1996 | Howland et al. |
| 5,505,734 A | 4/1996 | Caniggia |
| 5,507,745 A | 4/1996 | Logroscino et al. |
| 5,507,746 A | 4/1996 | Lin |
| 5,507,817 A | 4/1996 | Craig et al. |
| 5,509,933 A | 4/1996 | Davidson et al. |
| 5,514,132 A | 5/1996 | Csernatony et al. |
| 5,514,180 A | 5/1996 | Heggeness et al. |
| 5,516,335 A | 5/1996 | Kummer |
| 5,520,688 A | 5/1996 | Lin |
| 5,527,310 A | 6/1996 | Cole et al. |
| 5,531,792 A | 7/1996 | Huene |
| 5,531,793 A | 7/1996 | Kelman et al. |
| 5,538,427 A | 7/1996 | Hoffman et al. |
| 5,540,687 A | 7/1996 | Fairley et al. |
| 5,545,228 A | 8/1996 | Kambin |
| 5,549,608 A | 8/1996 | Errico et al. |
| 5,554,157 A | 9/1996 | Errico et al. |
| 5,569,247 A | 10/1996 | Morrison |
| 5,569,249 A | 10/1996 | James |
| 5,573,536 A | 11/1996 | Grosse et al. |
| 5,575,790 A | 11/1996 | Chen et al. |
| 5,582,612 A | 12/1996 | Lin |
| 5,584,833 A | 12/1996 | Fournet-Fayard et al. |
| 5,591,165 A | 1/1997 | Jackson |
| 5,591,166 A | 1/1997 | Bernhardt et al. |
| 5,591,167 A | 1/1997 | Laurain et al. |
| 5,591,169 A | 1/1997 | Benoist |
| 5,593,449 A | 1/1997 | Roberson, Jr. |
| 5,601,555 A | 2/1997 | Moskovich |
| 5,603,714 A | 2/1997 | Kaneda et al. |
| 5,603,715 A | 2/1997 | Kessler |
| 5,607,425 A | 3/1997 | Rogozinski |
| 5,607,430 A | 3/1997 | Bailey |
| 5,616,143 A | 4/1997 | Schlapfer et al. |
| 5,618,286 A | 4/1997 | Brinker |
| 5,620,445 A | 4/1997 | Brosnahan |
| 5,620,449 A | 4/1997 | Faccioli et al. |
| 5,624,441 A | 4/1997 | Sherman et al. |
| 5,626,579 A | 5/1997 | Muschler et al. |
| 5,626,580 A | 5/1997 | Brosnahan |
| 5,630,816 A | 5/1997 | Kambin |
| 5,630,817 A | 5/1997 | Rokegem et al. |
| 5,632,744 A | 5/1997 | Campbell, Jr. |
| 5,643,260 A | 7/1997 | Doherty |
| 5,643,261 A | 7/1997 | Schafer et al. |
| 5,643,262 A | 7/1997 | Metz-Stavenhagen et al. |
| 5,645,589 A | 7/1997 | Li |
| 5,645,599 A | 7/1997 | Samani |
| 5,647,872 A | 7/1997 | Gilbert et al. |
| 5,653,761 A | 8/1997 | Pisharodi |
| 5,653,762 A | 8/1997 | Pisharodi |
| 5,658,286 A | 8/1997 | Sava |
| 5,658,287 A | 8/1997 | Hofmann |
| 5,658,310 A | 8/1997 | Berger |
| 5,660,188 A | 8/1997 | Groiso |
| 5,662,651 A | 9/1997 | Tomier et al. |
| 5,667,506 A | 9/1997 | Sutterlin |
| 5,672,175 A | 9/1997 | Martin |
| 5,683,392 A | 11/1997 | Richelsoph et al. |
| 5,683,460 A | 11/1997 | Persoons |
| 5,697,934 A | 12/1997 | Huebner |
| 5,700,263 A | 12/1997 | Schendel |
| 5,702,391 A | 12/1997 | Lin |
| 5,702,445 A | 12/1997 | Branemark |
| 5,704,936 A | 1/1998 | Mazel |
| 5,707,372 A | 1/1998 | Errico et al. |
| 5,709,682 A | 1/1998 | Medoff |
| 5,713,898 A | 2/1998 | Stucker et al. |
| 5,713,900 A | 2/1998 | Benzel et al. |
| 5,713,903 A | 2/1998 | Sander et al. |
| 5,716,355 A | 2/1998 | Jackson et al. |
| 5,716,356 A | 2/1998 | Biedermann et al. |
| 5,716,358 A | 2/1998 | Ochoa et al. |
| 5,718,705 A | 2/1998 | Sammarco |
| 5,718,706 A | 2/1998 | Roger |
| 5,722,976 A | 3/1998 | Brown |
| 5,725,527 A | 3/1998 | Biedermann et al. |
| 5,741,254 A | 4/1998 | Henry et al. |
| 5,743,908 A | 4/1998 | Kim |
| 5,743,911 A | 4/1998 | Cotrel |
| 5,743,914 A | 4/1998 | Skiba |
| 5,759,184 A | 6/1998 | Santangelo |
| 5,769,850 A | 6/1998 | Chin |
| 5,769,897 A | 6/1998 | Harle |
| 5,776,135 A | 7/1998 | Errico et al. |
| 5,779,704 A | 7/1998 | Kim |
| 5,782,918 A | 7/1998 | Klardie et al. |
| 5,782,920 A | 7/1998 | Colleran |
| 5,785,711 A | 7/1998 | Errico et al. |
| 5,785,713 A | 7/1998 | Jobe |
| 5,791,899 A | 8/1998 | Sachdeva et al. |
| 5,800,433 A | 9/1998 | Benzel et al. |
| 5,800,434 A | 9/1998 | Campbell, Jr. |
| 5,810,815 A | 9/1998 | Morales |
| 5,810,816 A | 9/1998 | Roussouly et al. |
| 5,819,748 A | 10/1998 | Pfirrmann |
| 5,827,285 A * | 10/1998 | Bramlet ......................... 606/60 |
| 5,827,289 A | 10/1998 | Reiley et al. |
| 5,853,414 A | 12/1998 | Groiso |
| 5,855,579 A | 1/1999 | James |
| 5,868,747 A | 2/1999 | Ochoa et al. |
| 5,871,484 A | 2/1999 | Spievack et al. |
| 5,876,403 A | 3/1999 | Shitoto |
| 5,879,352 A | 3/1999 | Filosa et al. |
| 5,882,351 A | 3/1999 | Fox |
| 5,885,290 A | 3/1999 | Guerrero et al. |
| 5,891,145 A | 4/1999 | Morrison et al. |
| 5,895,387 A | 4/1999 | Guerrero et al. |
| 5,895,428 A | 4/1999 | Berry |
| 5,902,303 A | 5/1999 | Eckhof et al. |
| 5,906,573 A | 5/1999 | Aretz |
| 5,908,421 A | 6/1999 | Beger |
| 5,919,194 A | 7/1999 | Anderson |
| 5,921,986 A | 7/1999 | Bonutti |
| 5,928,231 A | 7/1999 | Klein et al. |
| 5,928,234 A | 7/1999 | Manspeizer |
| 5,928,267 A | 7/1999 | Bonutti et al. |
| 5,931,838 A | 8/1999 | Vito |
| 5,938,662 A | 8/1999 | Rinner |
| 5,941,878 A | 8/1999 | Medoff |
| 5,947,967 A | 9/1999 | Barker |
| 5,947,968 A | 9/1999 | Rogozinski |
| 5,950,633 A | 9/1999 | Lynch et al. |
| 5,951,554 A | 9/1999 | Holmes |
| 5,961,516 A | 10/1999 | Graf |
| 5,964,765 A | 10/1999 | Fenton, Jr. et al. |
| 5,968,098 A | 10/1999 | Winslow |
| 5,972,015 A | 10/1999 | Scribner et al. |
| 5,976,137 A | 11/1999 | Mayer |
| 5,980,522 A | 11/1999 | Koros et al. |
| 5,980,540 A | 11/1999 | Bruce |
| 5,980,973 A | 11/1999 | Onyekaba et al. |
| 5,984,922 A | 11/1999 | McKay |
| 5,989,250 A | 11/1999 | Wagner et al. |
| 5,993,449 A | 11/1999 | Schlapfer et al. |
| 5,997,539 A | 12/1999 | Errico et al. |
| 5,997,541 A | 12/1999 | Schenk |
| 6,001,098 A | 12/1999 | Metz-Stavenhagen et al. |
| 6,004,324 A | 12/1999 | Gahr |
| 6,007,536 A | 12/1999 | Yue |
| 6,007,538 A | 12/1999 | Levin |
| 6,008,432 A | 12/1999 | Taylor |
| 6,022,349 A | 2/2000 | Mcleod et al. |
| 6,024,759 A | 2/2000 | Nuss et al. |
| 6,027,533 A | 2/2000 | Olerud |
| 6,033,412 A | 3/2000 | Losken et al. |
| 6,034,296 A | 3/2000 | Elvin et al. |
| 6,039,762 A | 3/2000 | McKay |
| 6,045,551 A | 4/2000 | Bonutti |
| 6,045,579 A | 4/2000 | Hochshuler et al. |

(56) References Cited

U.S. PATENT DOCUMENTS

| | | |
|---|---|---|
| 6,063,089 A | 5/2000 | Errico et al. |
| 6,066,154 A | 5/2000 | Reiley et al. |
| 6,077,265 A | 6/2000 | Werding |
| 6,077,266 A | 6/2000 | Medoff |
| 6,080,154 A | 6/2000 | Reay-Young et al. |
| 6,096,079 A | 8/2000 | Eaton |
| 6,106,557 A | 8/2000 | Robioneck et al. |
| 6,113,599 A | 9/2000 | Landsberger |
| 6,117,160 A | 9/2000 | Bonutti |
| 6,120,503 A | 9/2000 | Michelson |
| 6,126,659 A | 10/2000 | Wack |
| 6,136,000 A | 10/2000 | Louis et al. |
| 6,146,384 A | 11/2000 | Lee et al. |
| 6,146,406 A | 11/2000 | Shluzas et al. |
| 6,162,255 A * | 12/2000 | Oyola .................. 623/20.34 |
| 6,171,310 B1 | 1/2001 | Giordano et al. |
| 6,174,311 B1 | 1/2001 | Branch et al. |
| 6,187,004 B1 | 2/2001 | Fearon |
| 6,197,029 B1 | 3/2001 | Fujimori |
| 6,200,316 B1 | 3/2001 | Zwirkoski et al. |
| 6,200,324 B1 | 3/2001 | Regni, Jr. |
| 6,203,543 B1 | 3/2001 | Glossop |
| 6,210,413 B1 | 4/2001 | Justis et al. |
| 6,214,006 B1 | 4/2001 | Metz-Stavenhagen |
| 6,217,578 B1 | 4/2001 | Crozet et al. |
| 6,221,073 B1 | 4/2001 | Weiss et al. |
| 6,221,074 B1 | 4/2001 | Cole et al. |
| 6,224,597 B1 | 5/2001 | Coker |
| 6,224,606 B1 | 5/2001 | Horiuchi |
| 6,231,576 B1 | 5/2001 | Frigg et al. |
| 6,235,033 B1 | 5/2001 | Brace et al. |
| 6,238,395 B1 | 5/2001 | Bonutti |
| 6,245,075 B1 | 6/2001 | Betz et al. |
| 6,248,104 B1 | 6/2001 | Chopin et al. |
| 6,254,602 B1 | 7/2001 | Justis |
| 6,258,089 B1 | 7/2001 | Campbell et al. |
| 6,273,888 B1 | 8/2001 | Justis |
| 6,280,442 B1 | 8/2001 | Barker et al. |
| 6,287,310 B1 | 9/2001 | Fox |
| 6,296,643 B1 | 10/2001 | Hopf et al. |
| 6,299,614 B1 | 10/2001 | Kretschmer et al. |
| 6,299,642 B1 | 10/2001 | Chan |
| 6,315,779 B1 | 11/2001 | Morrison et al. |
| 6,319,252 B1 | 11/2001 | McDevitt et al. |
| 6,319,255 B1 | 11/2001 | Grundei et al. |
| 6,322,562 B1 | 11/2001 | Wolter |
| 6,328,743 B2 | 12/2001 | Lerch |
| 6,336,928 B1 | 1/2002 | Guerin et al. |
| 6,336,930 B1 | 1/2002 | Stalcup et al. |
| 6,342,055 B1 | 1/2002 | Eisermann et al. |
| 6,346,123 B1 | 2/2002 | McKay |
| 6,355,039 B1 | 3/2002 | Troussel et al. |
| 6,355,041 B1 | 3/2002 | Martin |
| 6,364,881 B1 | 4/2002 | Apgar et al. |
| 6,364,882 B1 | 4/2002 | Orbay |
| 6,368,319 B1 | 4/2002 | Schaefer |
| 6,368,320 B1 | 4/2002 | Le Couedic et al. |
| 6,379,360 B1 | 4/2002 | Ackeret et al. |
| 6,387,096 B1 | 5/2002 | Hyde, Jr. |
| 6,402,753 B1 | 6/2002 | Cole et al. |
| 6,423,063 B1 | 7/2002 | Bonutti |
| 6,432,106 B1 | 8/2002 | Fraser |
| 6,432,108 B1 | 8/2002 | Burgess et al. |
| 6,440,131 B1 | 8/2002 | Haidukewych |
| 6,440,135 B2 | 8/2002 | Orbay et al. |
| 6,458,134 B1 | 10/2002 | Songer et al. |
| 6,461,360 B1 | 10/2002 | Adam |
| 6,485,493 B1 | 11/2002 | Bremer |
| 6,491,695 B1 | 12/2002 | Roggenbuck |
| 6,500,178 B2 | 12/2002 | Zucherman et al. |
| 6,503,251 B1 | 1/2003 | Shadduck |
| 6,506,191 B1 | 1/2003 | Joos |
| 6,508,819 B1 | 1/2003 | Orbay |
| 6,511,481 B2 | 1/2003 | von Hoffmann et al. |
| 6,514,257 B2 | 2/2003 | Dovesi et al. |
| 6,520,963 B1 | 2/2003 | McKinley |
| 6,524,314 B1 | 2/2003 | Dean et al. |
| 6,524,315 B1 | 2/2003 | Selvitelli et al. |
| 6,527,772 B2 | 3/2003 | Enayati |
| 6,540,746 B1 | 4/2003 | Buhler et al. |
| 6,547,564 B1 | 4/2003 | Hansson |
| 6,547,790 B2 | 4/2003 | Harkey, III et al. |
| 6,547,793 B1 | 4/2003 | McGuire |
| 6,547,794 B2 | 4/2003 | Auge', II |
| 6,558,389 B2 | 5/2003 | Clark et al. |
| 6,562,038 B1 | 5/2003 | Morrison |
| 6,565,565 B1 | 5/2003 | Yuan et al. |
| 6,569,165 B2 | 5/2003 | Wahl |
| 6,572,618 B1 | 6/2003 | Morrison |
| 6,572,620 B1 | 6/2003 | Schon |
| 6,575,975 B2 | 6/2003 | Brace et al. |
| 6,576,018 B1 | 6/2003 | Holt |
| 6,579,293 B1 | 6/2003 | Chandran |
| 6,579,294 B2 | 6/2003 | Robioneck |
| 6,585,738 B1 | 7/2003 | Mangione et al. |
| 6,592,587 B1 | 7/2003 | Roger |
| 6,596,009 B1 | 7/2003 | Jelic |
| 6,599,289 B1 | 7/2003 | Bojarski et al. |
| 6,607,548 B2 | 8/2003 | Pohjonen et al. |
| 6,610,062 B2 | 8/2003 | Bailey et al. |
| 6,613,052 B1 | 9/2003 | Kinnett |
| 6,616,665 B2 | 9/2003 | Grafton et al. |
| 6,629,975 B1 | 10/2003 | Kilpela et al. |
| 6,629,977 B1 | 10/2003 | Wolf |
| 6,632,503 B1 | 10/2003 | Shikinami et al. |
| 6,638,279 B2 | 10/2003 | Bonutti |
| 6,645,208 B2 | 11/2003 | Apfelbaum et al. |
| 6,645,210 B2 | 11/2003 | Manderson |
| 6,652,592 B1 | 11/2003 | Grooms et al. |
| 6,656,179 B1 | 12/2003 | Schaefer et al. |
| 6,660,005 B2 | 12/2003 | Toyama et al. |
| 6,660,022 B1 | 12/2003 | Li et al. |
| 6,673,073 B1 | 1/2004 | Schafer |
| 6,673,079 B1 | 1/2004 | Kane |
| 6,679,890 B2 | 1/2004 | Margulies et al. |
| 6,692,530 B2 | 2/2004 | Doubler et al. |
| 6,702,815 B2 | 3/2004 | Kuntz |
| 6,706,043 B2 | 3/2004 | Steiner et al. |
| 6,706,044 B2 | 3/2004 | Kuslich et al. |
| 6,709,434 B1 | 3/2004 | Gournay et al. |
| 6,711,432 B1 | 3/2004 | Krause et al. |
| 6,719,758 B2 | 4/2004 | Beger et al. |
| 6,719,801 B1 | 4/2004 | Holt |
| 6,723,095 B2 | 4/2004 | Hammerslag |
| 6,736,815 B2 | 5/2004 | Ginn |
| 6,736,818 B2 | 5/2004 | Perren |
| 6,740,086 B2 | 5/2004 | Richelsoph |
| 6,740,089 B2 | 5/2004 | Haider |
| 6,749,361 B2 | 6/2004 | Hermann et al. |
| 6,761,720 B1 | 7/2004 | Senegas |
| 6,770,073 B2 | 8/2004 | McDevitt et al. |
| 6,790,208 B2 | 9/2004 | Oribe et al. |
| 6,802,844 B2 | 10/2004 | Ferree |
| 6,805,716 B2 | 10/2004 | Ralph et al. |
| 6,832,999 B2 | 12/2004 | Ueyama et al. |
| 6,833,007 B2 | 12/2004 | Lob |
| 6,849,076 B2 | 2/2005 | Blunn et al. |
| 6,863,671 B1 | 3/2005 | Strobel et al. |
| 6,875,216 B2 | 4/2005 | Wolf |
| 6,902,566 B2 | 6/2005 | Zucherman et al. |
| 6,918,910 B2 | 7/2005 | Smith et al. |
| 6,932,841 B2 | 8/2005 | Sklar et al. |
| 6,949,123 B2 | 9/2005 | Reiley |
| 6,974,460 B2 | 12/2005 | Carbone |
| 6,979,333 B2 | 12/2005 | Hammerslag |
| 7,001,385 B2 | 2/2006 | Bonutti |
| 7,029,472 B1 | 4/2006 | Fortin |
| 7,033,399 B2 * | 4/2006 | Doubler et al. ............ 623/22.42 |
| 7,037,324 B2 | 5/2006 | Martinek |
| 7,056,322 B2 | 6/2006 | Davison et al. |
| 7,074,294 B2 | 7/2006 | Dubrow |
| 7,083,622 B2 | 8/2006 | Simonson |
| 7,083,638 B2 | 8/2006 | Foerster |
| 7,090,668 B1 | 8/2006 | U |

(56) References Cited

U.S. PATENT DOCUMENTS

| | | |
|---|---|---|
| 7,090,674 B2 | 8/2006 | Doubler |
| 7,094,236 B2 | 8/2006 | Waisman |
| 7,094,239 B1 | 8/2006 | Michelson |
| 7,101,374 B2 | 9/2006 | Hyde |
| 7,104,992 B2 | 9/2006 | Bailey |
| 7,115,143 B1 | 10/2006 | Michelson |
| 7,137,986 B2 | 11/2006 | Troxell |
| 7,156,847 B2 | 1/2007 | Abramson |
| 7,163,561 B2 | 1/2007 | Michelson |
| 7,169,149 B1 | 1/2007 | Hajianpour |
| 7,175,623 B2 | 2/2007 | Thramann |
| 7,189,251 B2 | 3/2007 | Kay |
| 7,192,445 B2 | 3/2007 | Ellingsen |
| 7,201,751 B2 | 4/2007 | Zucherman |
| 7,207,993 B1 | 4/2007 | Baldwin |
| 7,211,088 B2 | 5/2007 | Grafton |
| 7,214,225 B2 | 5/2007 | Ellis |
| 7,217,279 B2 | 5/2007 | Reese |
| 7,235,100 B2 | 6/2007 | Martinek |
| 7,261,714 B2 | 8/2007 | Richelsoph |
| 7,261,715 B2 | 8/2007 | Rezach |
| 7,261,716 B2 | 8/2007 | Strobel |
| 7,285,121 B2 | 10/2007 | Braun |
| 7,288,093 B2 | 10/2007 | Michelson |
| 7,291,153 B2 | 11/2007 | Glascott |
| 7,727,240 B1 | 6/2010 | Benton |
| 7,753,961 B2 | 7/2010 | Chen et al. |
| 8,167,947 B2 | 5/2012 | Ainsworth et al. |
| 8,328,807 B2 * | 12/2012 | Brigido .................. 606/64 |
| 2002/0055744 A1 | 5/2002 | Reiley |
| 2007/0016202 A1 * | 1/2007 | Kraft et al. ............. 606/62 |
| 2007/0239157 A1 | 10/2007 | Guillaume |
| 2007/0276382 A1 | 11/2007 | Mikhail et al. |
| 2008/0103506 A1 | 5/2008 | Volpi et al. |
| 2008/0183171 A1 | 7/2008 | Elghazaly et al. |
| 2008/0221577 A1 | 9/2008 | Elghazaly |
| 2008/0294164 A1 | 11/2008 | Frank et al. |
| 2009/0099571 A1 | 4/2009 | Cresina et al. |

OTHER PUBLICATIONS

European Search Report for European Application No. 09795207.1, European Patent Office, Munich, Germany, dated Mar. 31, 2014, 8 pages.

Written Opinion for European Application No. 09795207.1, European Patent Office, Munich, Germany, dated Mar. 2, 2015, 4 pages.

* cited by examiner

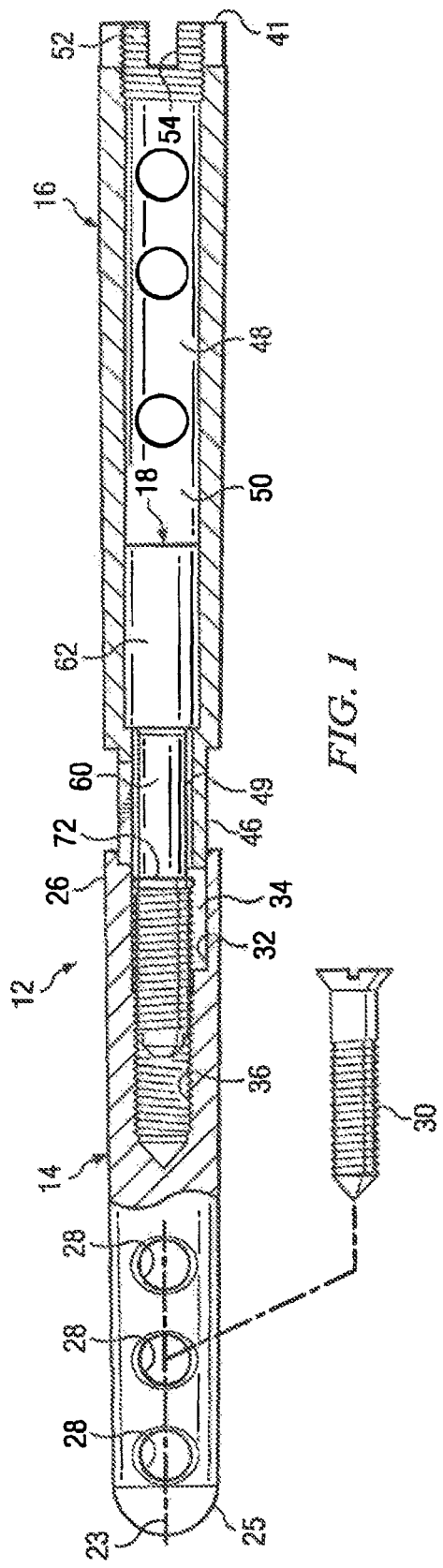
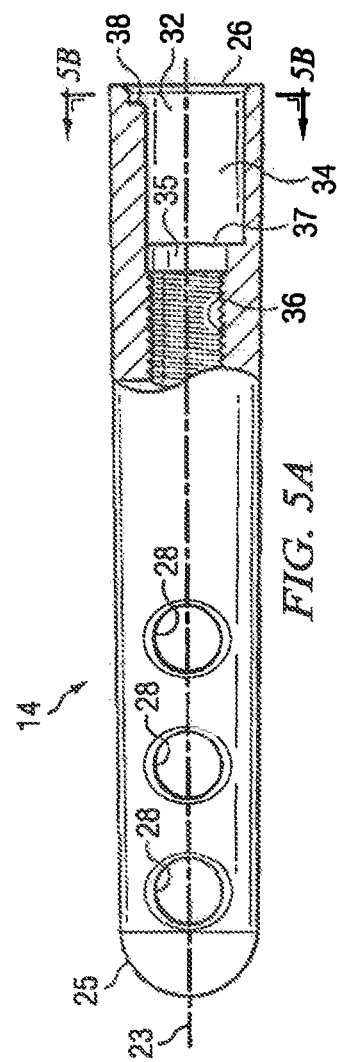
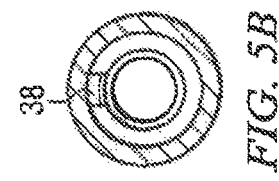

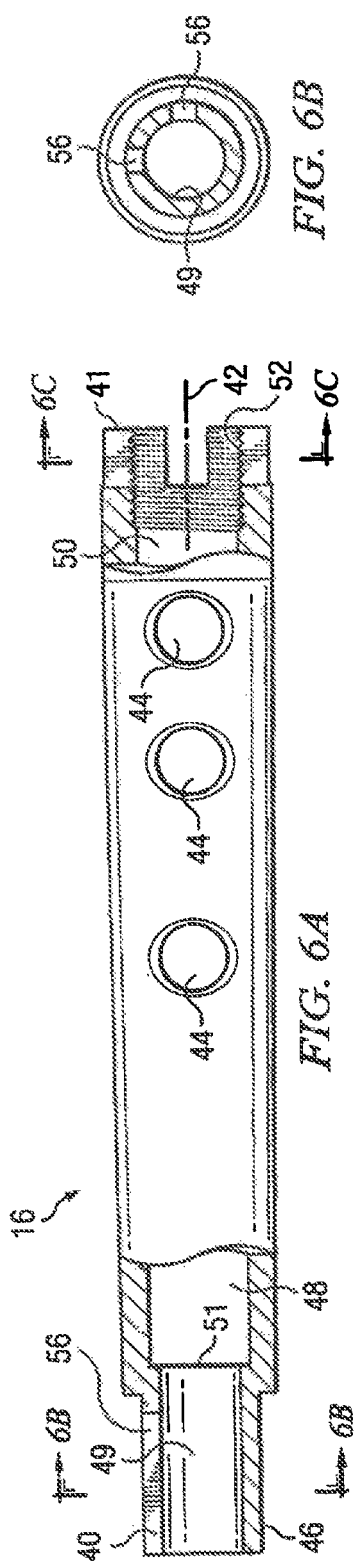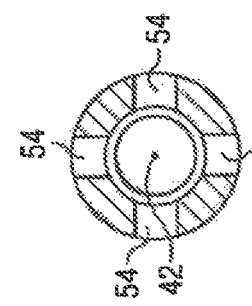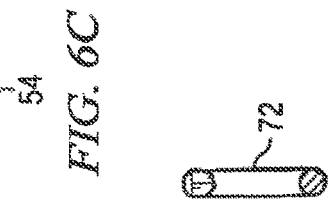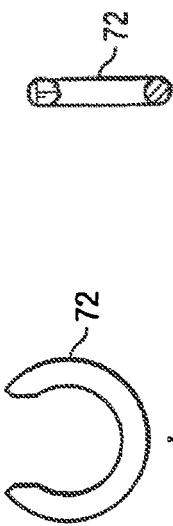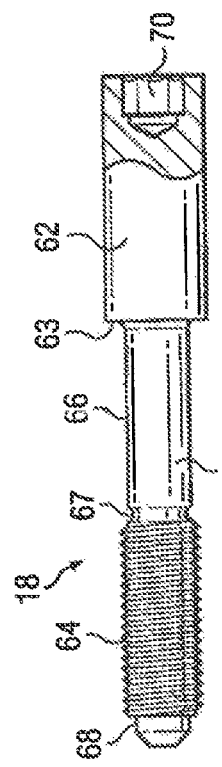

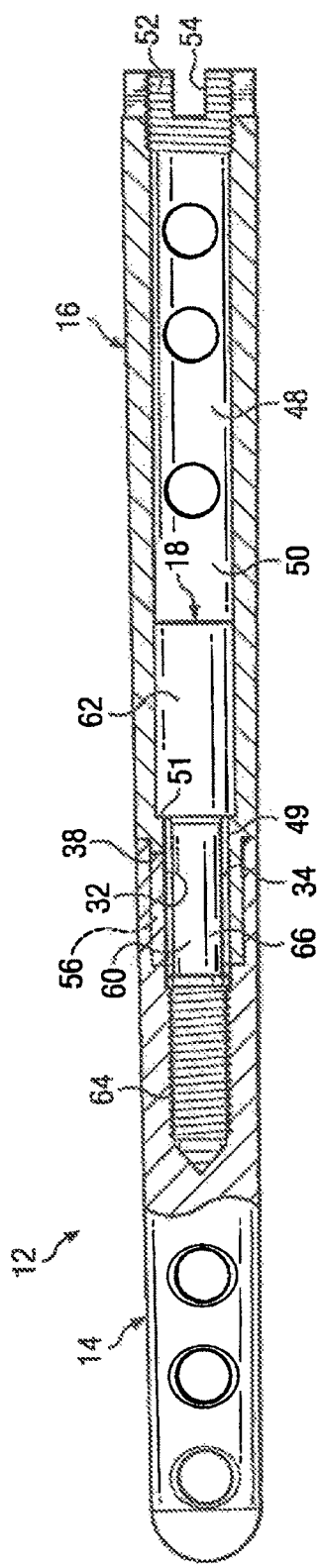
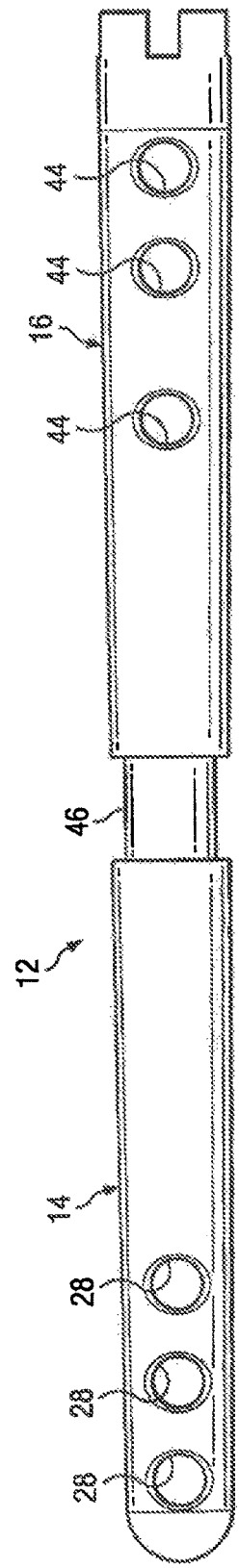
FIG. 9
FIG. 10A

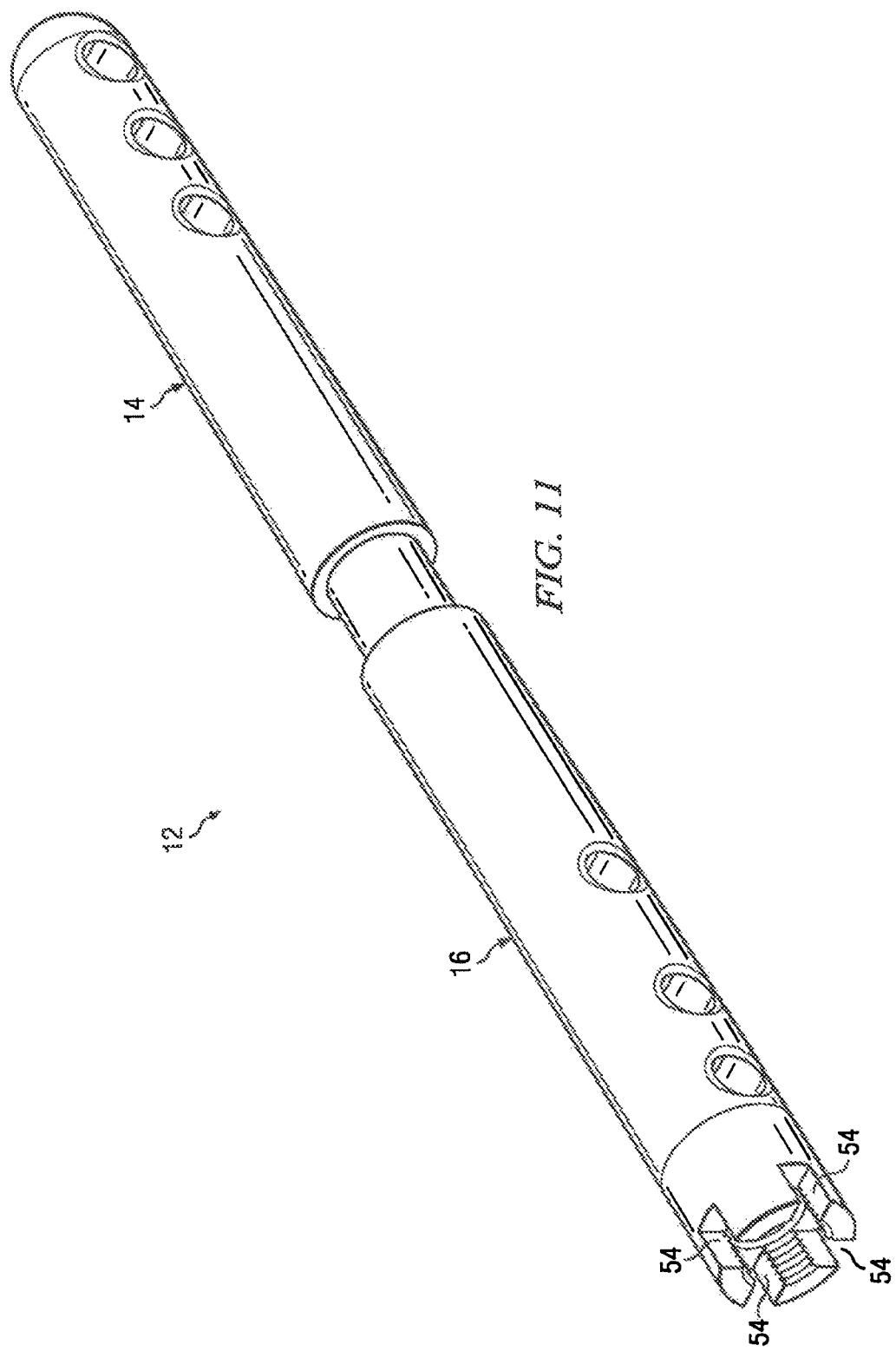

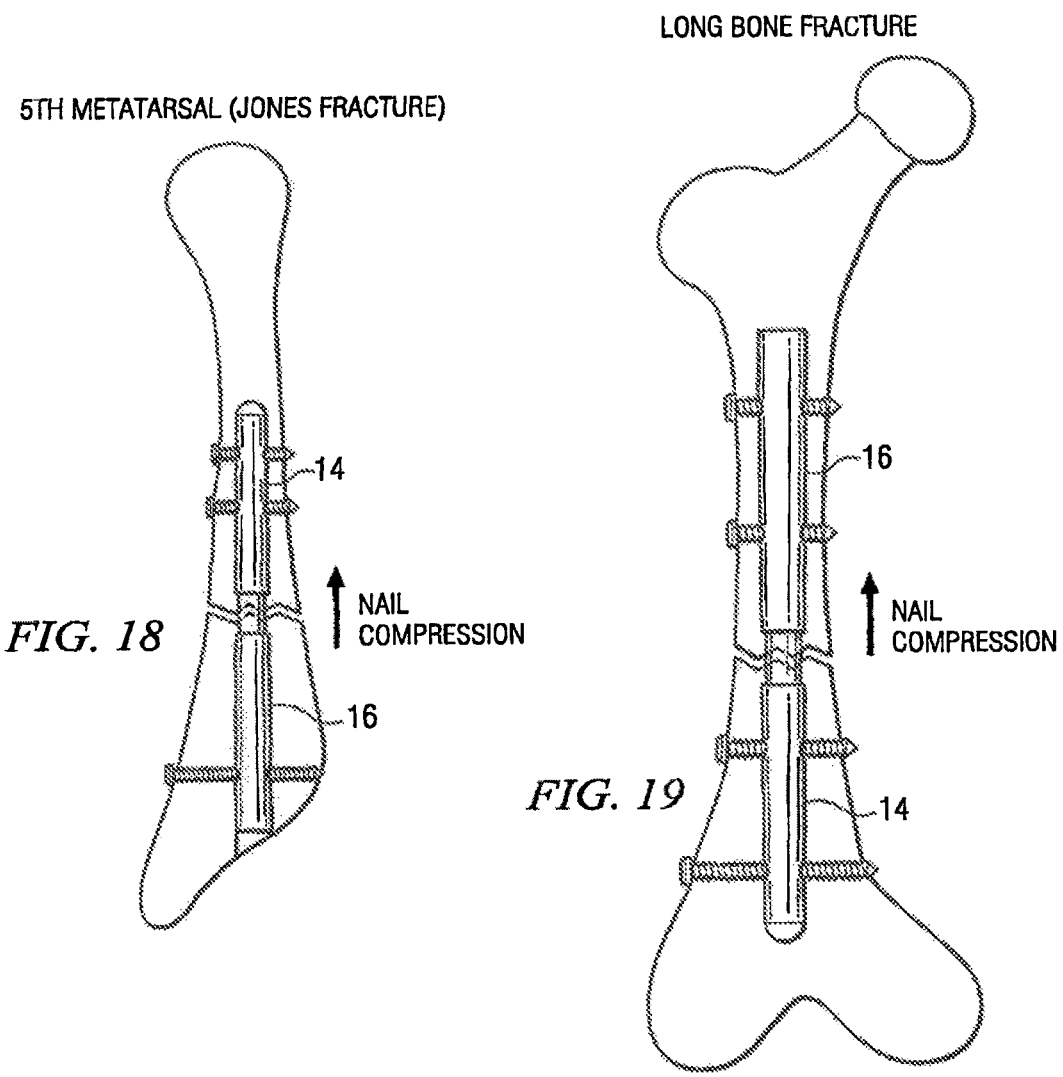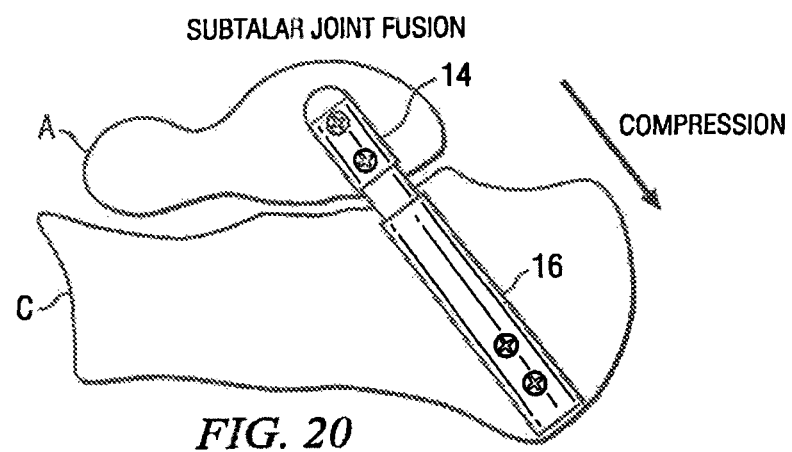

ANKLE ARTHRODESIS NAIL AND OUTRIGGER ASSEMBLY

CROSS-REFERENCE TO RELATED APPLICATIONS

This application is a continuation-in-part from and claims priority to U.S. patent application Ser. No. 12/500,473, filed on Jul. 9, 2009, entitled "ANKLE ARTHRODESIS NAIL AND OUTRIGGER ASSEMBLY," which claims priority to U.S. Provisional Application No. 61/079,132, filed on Jul. 9, 2008, entitled "ARTHRODESIS NAIL OUTRIGGER ASSEMBLY" and to U.S. Provisional Application No. 61/079,130 filed on Jul. 9, 2008, entitled "ANKLE ARTHRODESIS NAIL AND OUTRIGGER ASSEMBLY," all of which are incorporated herein by reference in their entirety as if set forth in full.

FIELD OF THE EMBODIMENTS

Embodiments of the present invention relate to surgical and bone fusion devices and systems in general, and more particularly to an improved arthrodesis nail that enables the bone fusion site to be sufficiently compression prior to fusion, and more particularly still tea an improved outrigger assembly and method for implanting an arthrodesis nail.

BACKGROUND

The lower limbs of the human body, namely the femur (thigh bone), the tibia (shinbone), and fibula, are designed to bear the weight of the body and to provide the body with sufficient stability. The femur courses medially from its proximal end connected to the hip bone to its distal end connected to the knee, placing the knee joints closer to the body's center of gravity and thus giving the body better balance while walking or standing. The tibia and fibula, which are connected together by an interosseous membrane, extend in parallel from the knee to ankle, with the tibia being larger and located medially in relation to the fibula. The tibia articulates proximally with the femur, forming the hinge joint of the knee, and distally with the talus bone of the foot at the ankle, and as such receives most of the body's weight and transmits it to the foot, while the fibula, which articulates proximally and distally with the lateral aspects of the tibia, is a non-weight bearing bone and generally provides stability for the ankle joint. The shaft of the tibia is generally triangular in cross section, and its distal end is blunt where it articulates with the talus. Situated medially to such distal tibia end is the medial malleolus, and a fibular notch is provided on the lateral surface of the tibia opposite the medial malleolus.

The foot skeleton is made up of the tarsus, metatarsus, and phalanges bones, with the tarsus bones forming the proximal or heel end of the foot, the metatarsus bones forming the bases of the toes, and the phalanges being the toe bones. The tarsal bones include the talus, calcaneus, lateral cuboid, medial navicular, and medial, intermediate, and lateral cuneiform bones. The talus articulates with the tibia and fibula superiorly and is located on the upper surface of the calcaneus bone, which forms the heel and with the part that touches the ground the tuber calcanei, and such bones support most of the weight of the body, although some weight is distributed to the heads of the metatarsals by the arching of the foot. In some patients the ankle joint or interconnection of the lower end of the tibia, the fibula, and the talus (spaced apart by articular cartilage and held together by various ligaments) can become worn or injured due to a degenerative condition or deformity, or a fracture, subluxation, or other traumatic event. In order to stabilize the ankle joint and control the often severe pain caused by such conditions, an arthrodesis procedure may be necessary to fuse and therefore permanently immobilize the ankle joint, fusing the distal end of the tibia with the talus. Where both the tibi-talar and talocalcaneal joints are damaged, such as in some patients having severe osteoporosis, the calcaneus bone will also be fused with the ankle. Such tibio-talacalcaneal arthrodesis procedures today are typically accomplished by permanent intramedullary nailing, wherein after the ankle bone surfaces have been prepared a rigid nail or rod is inserted in a hole drilled upwardly through the calcaneus and talus bones and into the medullary canal of the tibia. Screws are passed laterally through holes drilled in the tibia to hold the proximal end of the nail in place in the tibia, and into the nail through holes drilled in the calcaneus and talus bones. A limitation of known intramedullary or tibio-calcaneal arthrodesis nailing systems is in obtaining sufficient compression across the arthrodesis site so that a proper fusion is accomplished.

Embodiments of the invention provide both an arthrodesis implant which is simple, easy to install and effective, as well as an arthrodesis outrigger assembly for use with such implant which is effective during an arthrodesis operation for proper alignment and implantation of the arthrodesis implant.

Alternate embodiments also provide an arthrodesis implant which can be relatively easily implanted in the foot and ankle and quickly, easily and effectively secured in place.

Alternate embodiments also provide an arthrodesis prosthesis which is formed in two main sections which are adjustably secured together by an intervening rotatable adapter effective from the bottom of the arthrodesis prosthesis to compress or place tension on the leg and ankle bones to be fused.

Alternate embodiments also provide an arthrodesis implant which is formed in two main sections adjustably secured together by a central rotating fitting which in combination with an external compression disc are used to provide tension from and through the foot bone to provide compression of the bones in an arthrodesis site prior to insertion of retaining screws used to immobilize the foot bones after which the compression disc can be removed.

Alternate embodiments also provide an improved arthrodesis nail outrigger assembly adapted for guiding an arthrodesis tool into the foot and leg bones applying an external compression disc and retaining screws after which the outrigger assembly can be removed.

Alternate embodiments also provide an arthrodesis nail outrigger assembly wherein the outrigger assembly can be adjustably rotated around an arthrodesis with respect to a stationary intramedullary nail device.

Alternate embodiments also provide an arthrodesis nail outrigger assembly having a cannulated nail mounting shaft arrangement to allow for compression of a two-sectioned intramedullary nail device, resulting in a more tightly compressed and stable tibio-calcaneal arthrodesis.

Objects and advantages of embodiments of the invention will become clear upon review of the following detailed description in conjunction with the appended drawings.

SUMMARY

In a preferred embodiment, an intramedullary fastener or nail is provided, wherein the nail is formed in two sections that are adjustably joined together by an internal bolt member that can be rotated to decrease the total length of the combined nail. Accordingly, the device is capable of providing compression across an arthrodesis site in a tibio-calcaneal arthrodesis nailing procedure. After the nail has been inserted upwardly through holes drilled in the calcaneus and talus bones and tibia, using an outrigger assembly the nail may be secured to the tibia. After this the outrigger assembly, in combination with a compression disc provided at the distal end of the nail, can rotate the internal bolt member causing the distal or lower section of the nail and compression disc to move upwardly toward the proximal or upper section, thus providing compression of the calcaneus and talus bones with the tibia so that any spaces between the joints are closed prior to securing the bones in such position. In an alternate embodiment, at improved outrigger assembly is also provided that enables the outrigger handle to be rotated and secured at ninety-degree angles with respect to the stationary intramedullary nail. The outrigger assembly provides stability and ease of use. The outrigger assembly can include a cannulated nail mounting shaft that enables a compression driver to be inserted through the shaft upwardly into the nail to adjust the position of the belt member and provide the desired amount of compression across the arthrodesis site. In addition the amount of compression across the arthrodesis site can be adjusted at a later date via a minimally invasive procedure.

BRIEF DESCRIPTION OF THE DRAWINGS

FIG. 1 is a partial cross-sectional view an embodiment of the intramedullary fixation device along its longitudinal axis in an uncompressed configuration.

FIG. 5A is a side view of an embodiment of the proximal section of the intramedullary fixation device.

FIG. 5B is a cross-sectional view of the proximal section of an embodiment of the intramedullary fixation device of FIG. 5A.

FIG. 6A is a side view of an embodiment of the distal section of the intramedullary fixation device.

FIG. 6B is a view of an embodiment of the distal section of the intramedullary fixation device taken along the line B in FIG. 6A.

FIG. 6C is a view of an embodiment of the distal section of the intramedullary fixation device taken along the line C in FIG. 6A.

FIG. 7 is a side view of an embodiment of the compression bolt member of the intramedullary fixation device.

FIG. 8A is a side view of an embodiment of the bolt retainer member.

FIG. 8B is a cross-sectional view of the bolt retainer member shown in FIG. 8A.

FIG. 9 is a cross-sectional view of an embodiment of the intramedullary fixation device as shown in FIG. 1 in a compressed configuration.

FIG. 10A is a side view of an embodiment of the intramedullary fixation device in an uncompressed configuration.

FIG. 11 is a proximal end view of an embodiment of a section of the intramedullary fixation device.

FIG. 18 is a side view of an embodiment of the intramedullary fixation device as applied to an fifth metatarsal fracture in an uncompressed configuration.

FIG. 19 is a side view of an embodiment of the intramedullary fixation device as applied to an long bone fracture in an uncompressed configuration.

FIG. 20 is a side view of an embodiment of the intramedullary fixation device as applied to subtalar joint fusion in an uncompressed configuration.

DETAILED DESCRIPTION

This description is not intended to be understood in a limiting sense, but to be embodiments of the invention presented solely for illustration thereof, and by reference to, in connection with the following description and the accompanying drawings, one skilled in the art may be advised of advantages and construction of embodiments of the invention. Embodiments of the invention are intended to cover alternatives, modifications, and equivalents, which may be included within the spirit and scope of the invention as defined by the appended claims.

Figure 15:
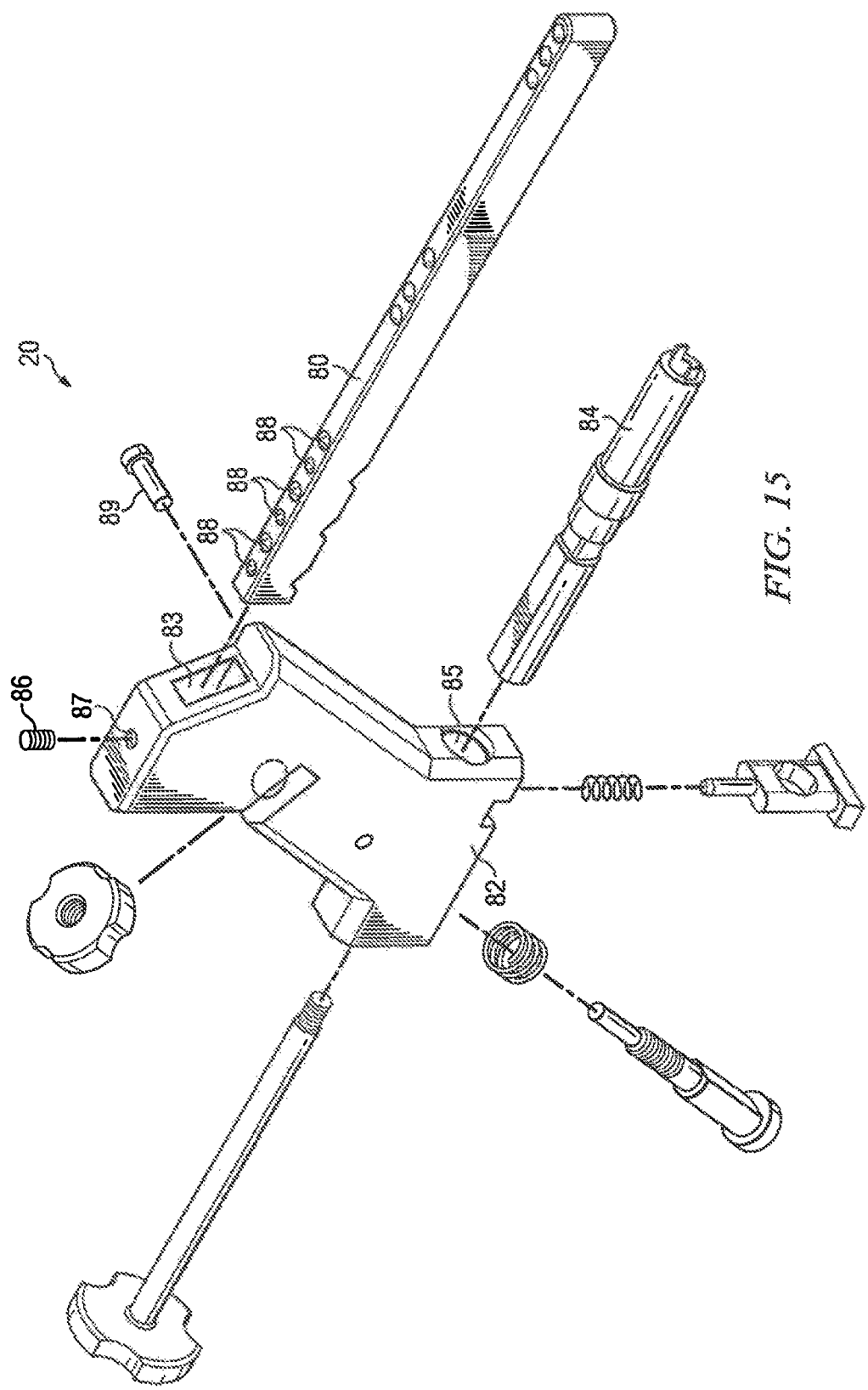
FIG. 15 is an exploded view from the side of an embodiment of the outrigger assembly.
Figure 16:
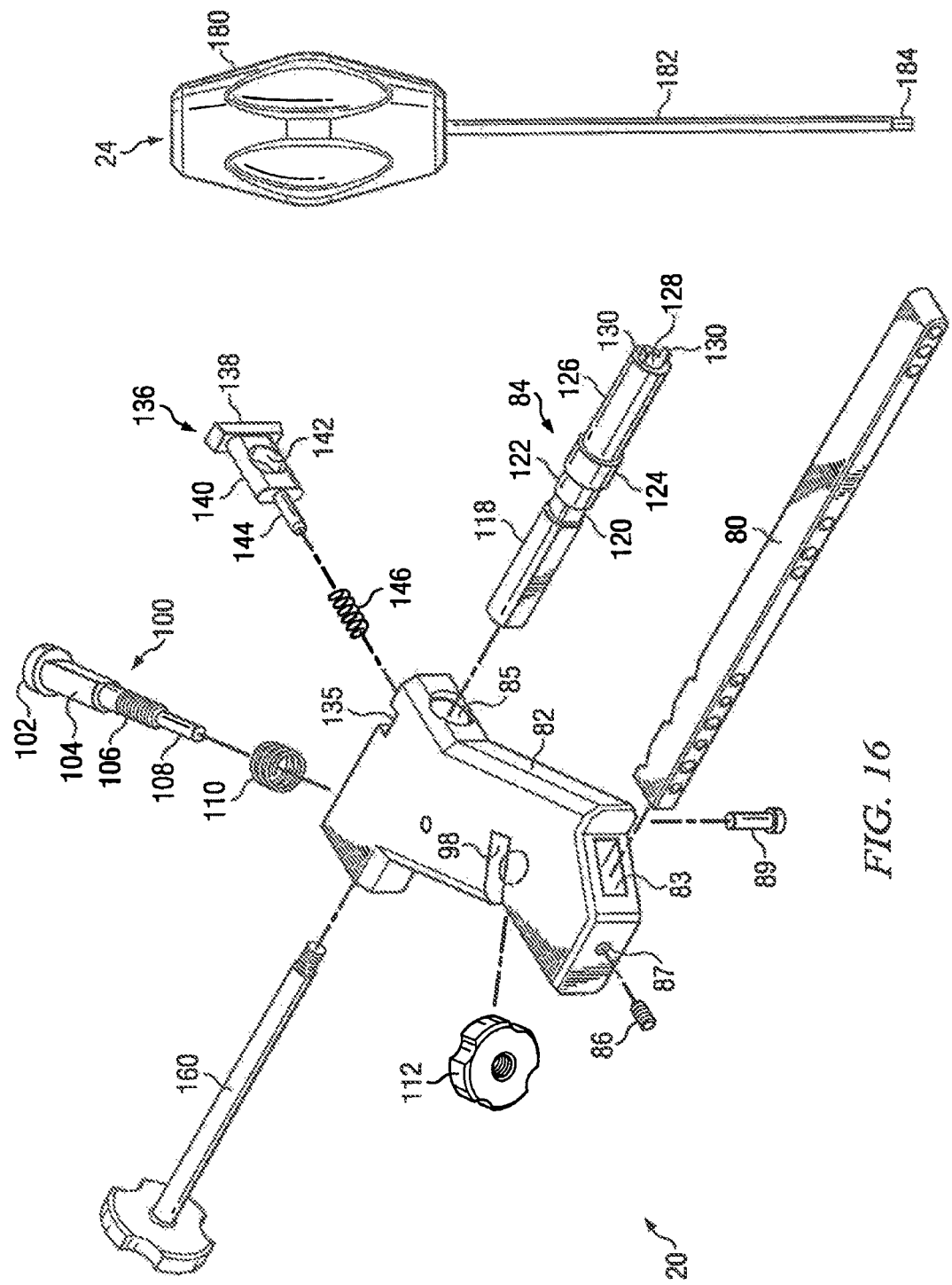
FIG. 16 is an exploded view from the top of an embodiment of the outrigger assembly.

FIGS. 1-11 illustrate embodiments of the intramedullary fixation device, FIGS. 12-14 and 17 illustrate embodiments of the combination intramedullary fixation device and outrigger assembly, and FIGS. 15-16 illustrate embodiments of the outrigger assembly alone. Referring to FIG. 1, there is shown an embodiment of the intramedullary fixation device 12 for stabilizing the position of and fusing together the tibia T (shin bone) relative to the talus A (adjoining ankle) and calcaneus C (heel) bones, and which is to be inserted through the bottom of the foot into the medullary canal of the tibia. Intramedullary nail 12 is comprised of two main sections, referred to generally herein as proximal section 14 and distal section 16. In addition, compression bolt 18 (see FIG. 7) can be used to join proximal section 14 to distal section 16, and provide the required tension or compression of the ankle joint on installed, as will also be described in detail below. In addition, alignment outrigger device 20 (FIG. 16) is provided, which can be used to precisely position nail 12 in the tibia T and fixed to the talus A and calcaneus C bones. Also shown in FIG. 16 is compression driver 24, which is used to adjust compression bolt 18.

Proximal 14 and distal 16 sections of intramedullary nail 12 generally have a rounded or circular shape, and are preferably made of surgical stainless steel or surgical stainless titanium, and correspond generally to the shape of the tibia medullary canal. Referring more particularly now to FIG. 5A, proximal section 14 of nail 12 has a forward end 25 and a rearward tad 26, and is slightly tapered along its longitudinal axis 23 from rearward end 26 to forward end 25, the outer surface of which end is preferably smooth and rounded. Through-holes 28 can be formed in the nail 12 extend perpendicular to longitudinal axis 23, and may be spaced apart in the shaft of proximal section 14 near forward end 25. Support screws 30 (see FIG. 1) can be passed through the holes 28 to secure proximal section 14 of nail 12 to the tibia bone in position in the tibia medullary canal. The screws 30 may have different lengths and sizes as required and known to those skilled in the art. The proximal section 14 of the nail 12 may further include a bore 32 that extends inwardly from the rearward end 26 of proximal section 14 along the longitudinal axis 23, forming non-threaded sleeve area 34 adjacent rearward end 26, a short non threaded section 35 adjacent sleeve area 34 and having a smaller diameter than sleeve area 34, with inwardly extending circumferential bearing surface 37 formed between areas 34 and 35. An internal screw threaded area 36 for receiving compression bolt 18 can be formed by extending inwardly from short section 35. See also FIGS. 1 and 9. In addition, at least one alignment tab 38 is provided in sleeve area 34.

Figure 10B:
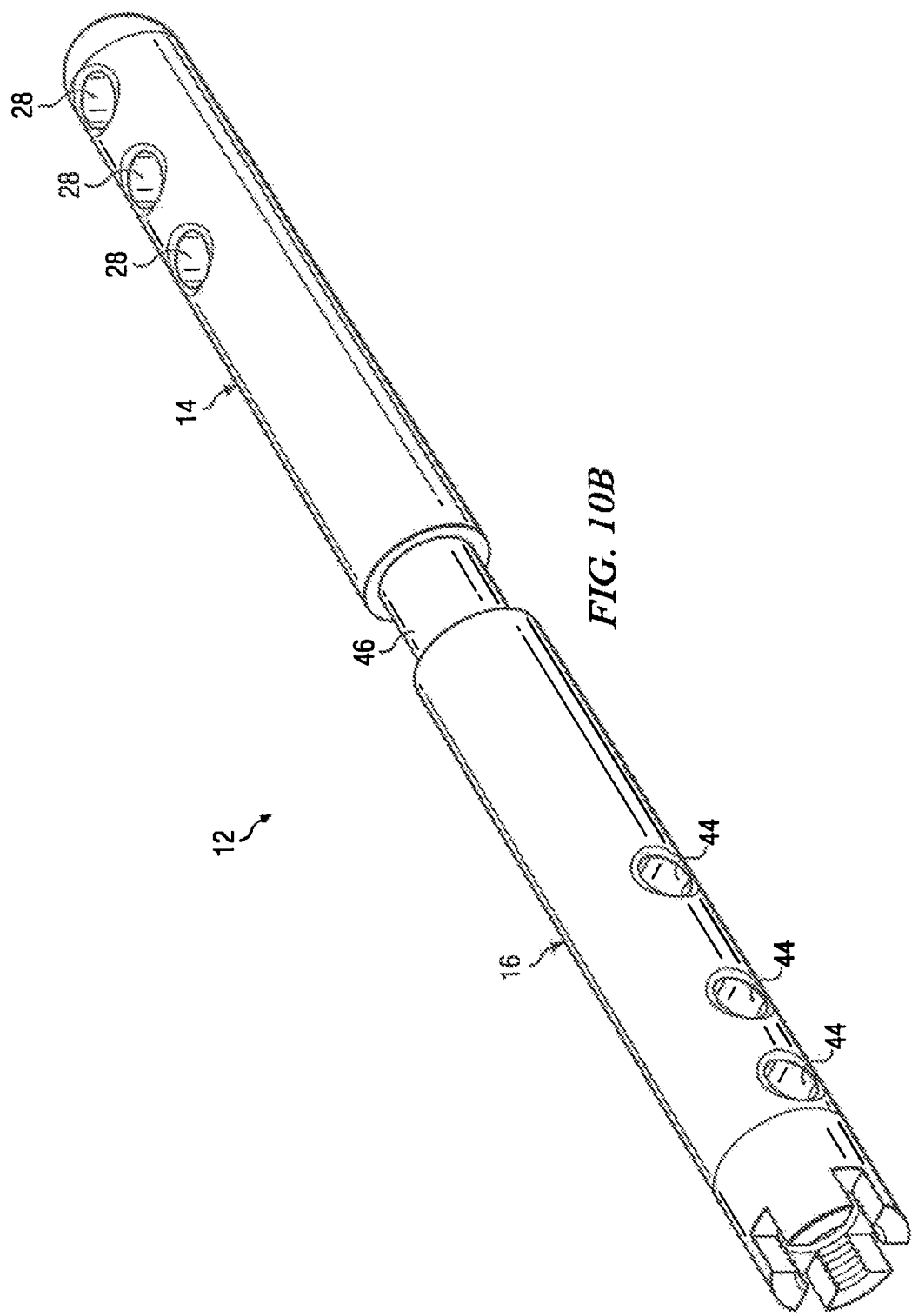
FIG. 10B is a side view of an alternative embodiment of the intramedullary fixation device.
Figure 12:
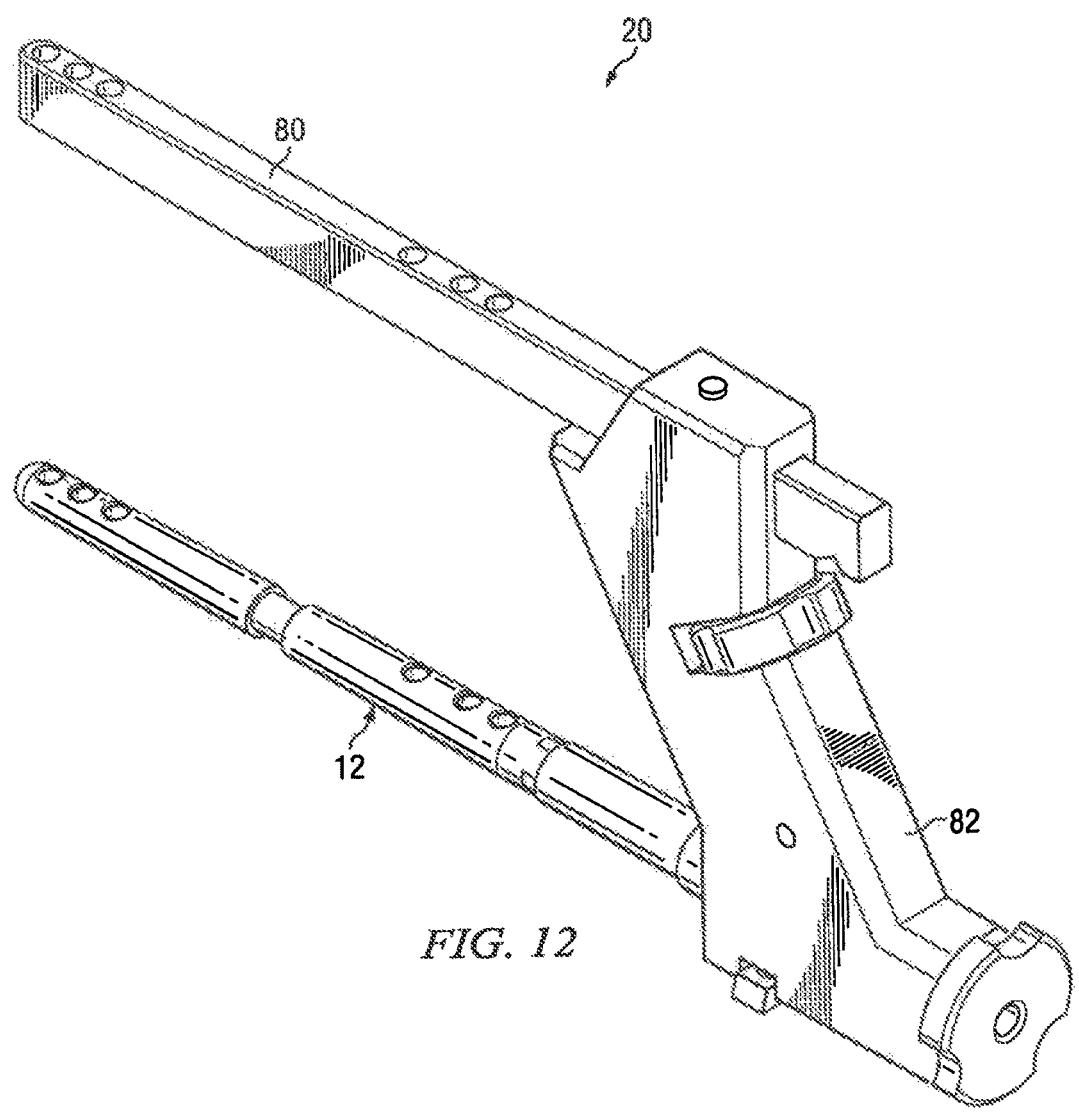
FIG. 12 is a perspective view from the side of an embodiment of the outrigger assembly and intramedullary fixation device.
Figure 13:
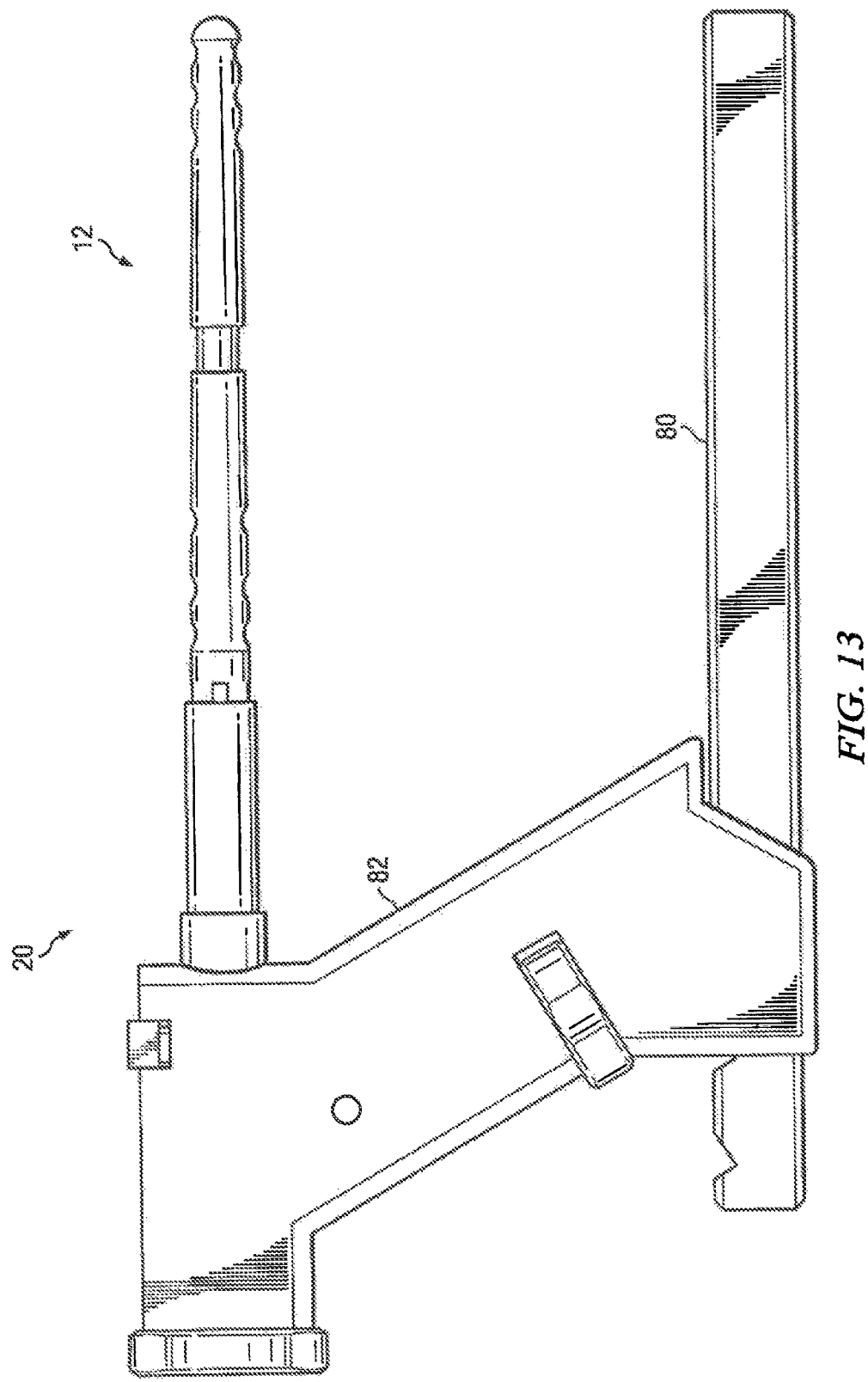
FIG. 13 is a side view of an embodiment of the outrigger assembly and intramedullary fixation device.
Figure 14:
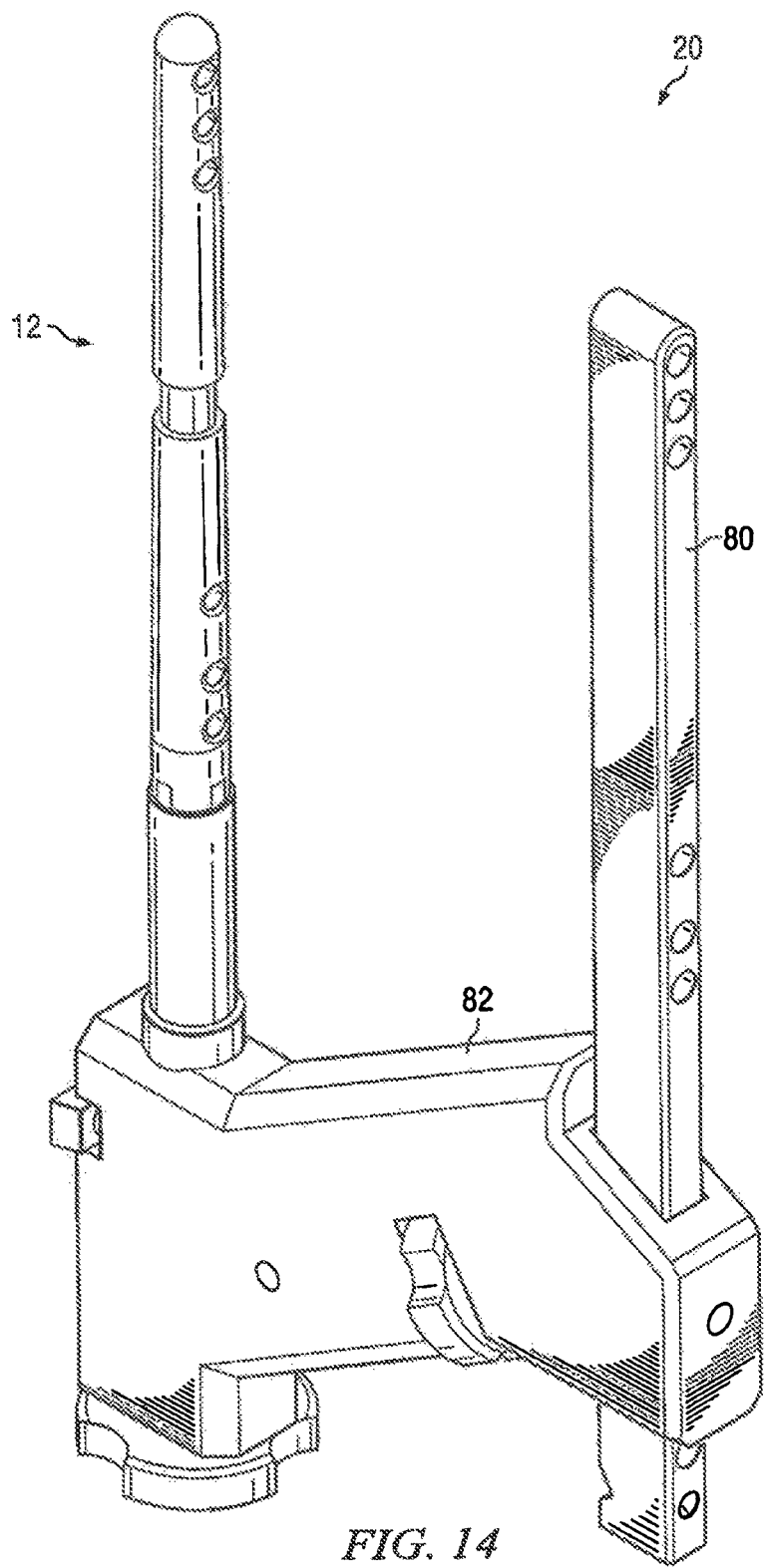
FIG. 14 is a perspective view from the top of an embodiment of the outrigger assembly and intramedullary fixation device.

As shown in FIG. 6A, distal section 16 of nail 12 has an upper end 40 and a lower end 41, and is preferably slightly tapered from lower end 41 to upper end 40 along its longitudinal axis 42. A plurality of holes 44 can be situated in distal section 16 near lower end 41 extending perpendicular to longitudinal axis 42 and spaced apart a predetermined distance, for receiving screws 30 passed through the talus and calcaneus bones. Situated on the upper end 40 of distal section 16 is arm 46 having a reduced outer diameter and being sized to be slidingly received in sleeve 34 of bore 32 in proximal section 14. A bore 48 extends through distal section 16 from upper end 40 to lower end 41, which bore 48 has a smaller diameter section 49 adjacent upper end 40 and arm 46, and a larger diameter section 50, with inwardly extending bearing surface or end wall 51 between such sections. The bore 48 is also variable in FIGS. 1 and 9. Threads 52 are provided in the inner walls of larger diameter section 50 of bore 48 adjacent lower end 41, while a plurality of spaced apart rectangular notches 54 are formed in lower end 41 (See FIGS. 6C and 11). The upper end 40 of distal section 16 includes two longitudinally-oriented notches 56. According to one embodiment, these notches are placed orthogonally with respect to each other and are aligned with or are orthogonal to the holes 44. The notches 56 are designed to mate with tab 38 in the rearward end of the proximal section 14 of the nail 12 as shown FIG. 5B. By providing two notches 56 in the upper end 40 of the distal section 16, the distal section can be oriented such that its holes 28 are either aligned with the holes 44 in the distal section 16, or placed orthogonal to holes 44. In this manner, the nail device 12 can be configured such that the nails can be applied uniformly in a medial-lateral (M-L) or anterior-posterior (A-P) direction, or distal nails and proximal nails can be alternated between an M-L, and A-P alignment (i.e., orthogonally), as shown in FIG. 10B.

Bore 48 is sized to receive compression bolt 18, shown in FIG. 7, which bolt has a reduced diameter section 60 and a larger diameter head section 62, forming an outwardly extending bearing surface 63 between sections 60 and 62. Reduced diameter section 60 includes a threaded section 64, a non-threaded shall section 66, a shallow notch 67 situated between such sections, and head section 68. A socket 70 is provided in the end surface of enlarged diameter section 62 to facilitate rotating bolt 18 in either a clockwise or counter-clockwise direction using a driving device 24 as described in more detail below. As shown in FIGS. 1 and 9, head section 62 of compression bolt 18 is sired to be received in bore 50 of distal section 16 of nail 12, while at the same time reduced diameter section 60 of bolt 18 is passed through bore sections 50, with threaded section 64 extending outwardly through forward end 40 while shaft section 66 remains in bore 49 in arm 46. When arm 46 is inserted in sleeve 34, male threaded section 64 can be received on the female threads in bore section 36, and when rotated on the threads arm 46 is pulled towards sleeve 34 until hearing surface 63 of head section 62 engages against beating surface 51 in bore 50. Compression bolt 18 can be adjustably secured to proximal section 14 by clip 72, shown in FIG. 8, which clip is secured around the outer surface of bolt 18 in slot 67, to prevent threaded section 64 from being moved out of bore 32 past sleeve section 34.

Embodiments of the invention also includes an improved outrigger assembly 20, shown alone in FIGS. 15-16, and with nail 12 attached in FIGS. 12-14 and 17. The outrigger assembly 20 is used to position and align the intramedullary fixation device 12 while it is being inserted and secured in the patient's tibia medullary canal, and also while a compressive force is applied across the arthrodesis site. Outrigger assembly 20 includes an alignment beam 80 that can be detachably and adjustably secured to handle 82 in a slot 83 along one side edge of handle 82 so that the beam extends outwardly from the handle. A nail engaging shaft 84 can be secured to handle 82 in an aperture 85 along the opposite side edge of the handle, so that which nail 12 is engaged with shaft 84, the nail 12 is spaced apart from and in parallel with beam 80. Outrigger assembly 20 is preferably made of carbon fiber, which is radiolucent and thus does not appear in x-rays, although other materials such as surgical stainless steel may be used.

Beam 80 can be secured in slot 83 by two different locking mechanisms on opposite sides of the slot. The first of these is a threaded pin 86 which is threadably secured in an aperture 87 in handle 82. A aperture 87 extends laterally between the outer side surface of handle 82 and slot 83. Thus, when pin 86 is inserted and tightened in aperture 87 with beam 80 in slot 83, its forward end extends through aperture 87 and presses against the side surface of beam 80, preferably in one of several notches 88 (see FIG. 17) in the corresponding side surface of beam 80, to hold it in place in slot 83. The second locking mechanism is pinstop 89, which engages with beam 80 provided on the opposite side of slot 83 in handle 82. As shown in the cross sectional view in FIG. 17, an angled aperture 90 is provided in handle 82 having a larger diameter end section 92, a reduced diameter center section 94, and second reduced diameter section 9 terminating at slot 83. In addition, a transverse slot 98 can be cut a out in handle 82 extending through reduced diameter center section 94. Aperture 90 can receive a lock shaft 100 having a head section 102, a non-threaded shaft section 104, a threaded shaft section 106, and a forward non-threaded pin section 108. Head section 102 is sized to be received in end section 92 of aperture 90, shaft sections 104 and 106 are sized to be received in center section 94 of aperture 90, and pin section 108 is sized to be received in section 96 of aperture 90. Lock spring 110 is placed around non-threaded shaft section 104, while adjustor knob 112 is secured over threaded shaft section 106 in transverse slot 98, such that taming knob 112 causes lock shaft 100 to move either forwardly or rearwardly in aperture 90, with the forward end of pin section 108 extending into one of several similarly angle apertures 114 in beam 80, thereby locking beam 80 in place. Notches 116 aligned with apertures 114 are also provided in beam 80, which when aligned properly with handle 82 engage teeth 117 on the inner surface of slot 83 adjacent second reduced diameter section 96 of aperture 90. Thus, the tension on beam 80 can be adjusted on one side by rotating knob 112, and on the other side using threaded pin 86 to ensure that such tension is generally equal and further than beam 80 is locked in place.

The intramedullary fixation device mounting shaft 84 may include a bottom section 118 that is generally square or rectangular and fits in aperture 85 in handle 82. The mounting shaft 84 also includes a slide lock receiving section 120, adjacent to bottom section 118, a short conical section 122 adjacent to slide lock receiving section 120, a second short enlarged diameter section 124 adjacent conical section 122, and a shaft section 126 for engaging with nail 12. A Cavity 128 may extend through the nail mounting shaft 84, and alignment tabs 130 that engage with notches 54 in the outer end 41 of distal section 16 of nail 12. The alignment tabs 130 also engaged with notches 154 on compression disc 150, shown in FIG. 4. The alignment tabs 130 can be provided on the outer end of shaft section 126. Another slot 134 and associated notch 135 (see FIG. 17) are provided in the side surface of handle 82 adjacent aperture 85, in which slide lock device 136 can be inserted. Slide lock device 136 has a head or button section 138, a rectangular shaft section 140 having a lateral through-hole 142, and a pin section 144 extending forwardly from shaft section 140, around which pin 144 coil spring 146 may be secured. When bottom section 118 of nail mounting shaft 84 is inserted in aperture 85, the slide lock device 136 can be inserted in aperture 134 unfit lateral hole 142 is aligned with aperture 85. Bottom section 118 may therefore be passed through lateral hole 142, and slide lock receiving section 120, which section has a width that is slightly greater than the width of shaft section 140, is aligned in hole 142. Slide lock device 136 can serve as a position stop locking device, as spring 146 causes shaft section 140 to press against the side surface of slide lock receiving section 120, thereby locking nail receiving shaft 84 in place secured to handle 82. When button 138 on slide lock device 136 is pressed inwardly, shaft 84 is released and outrigger assembly 20 can be swiveled or rotated with respect to shaft 84 and nail 12 in a three hundred sixty degree range around shaft 84 and nail 12. The outrigger assembly 20 can also be stopped and locked at ninety degree intervals. Such unique feature enables the outrigger assembly to be rotated to different positions or angles around a patient's legs as desired, with the nail 12 remaining stationary or fixed to the patient's tibia. This may be desired in some cases where the outrigger assembly is in the surgeon's way while another step or task is being performed, and allows the assembly to be moved out of the way and then back again after a task has been completed, or where the outrigger assembly must be moved in order to complete the operation.

Figure 2:
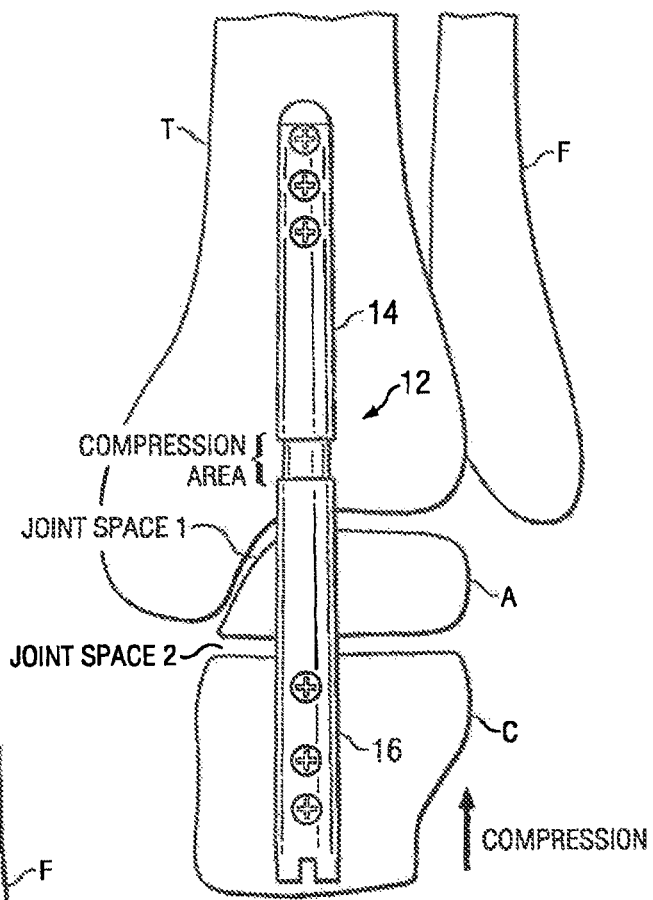
FIG. 2 is a side view of an embodiment of the intramedullary fixation device as applied to an ankle joint in an uncompressed configuration.
Figure 3:
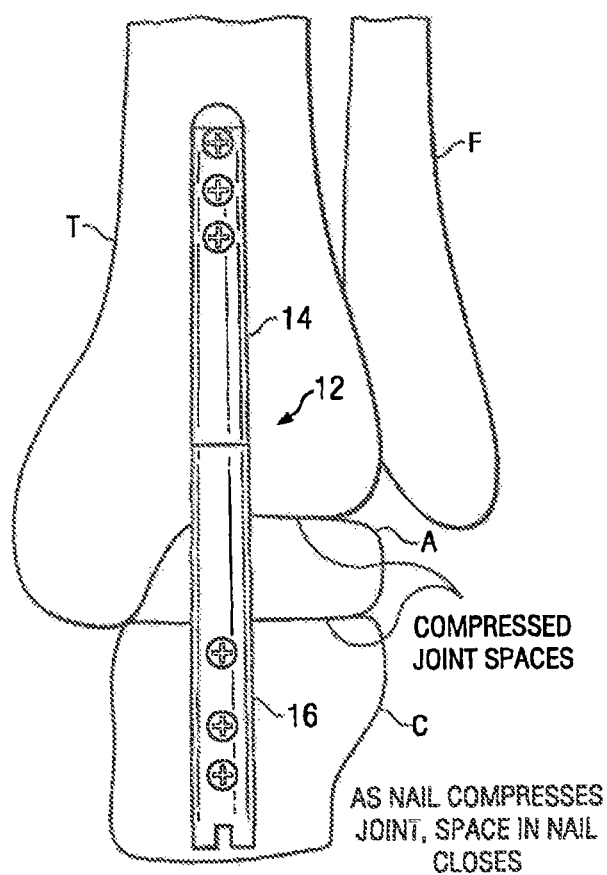
FIG. 3 is a side view of the fixation device shown in FIG. 2 as applied to an ankle joint in a fully compressed configuration.
Figure 4A:
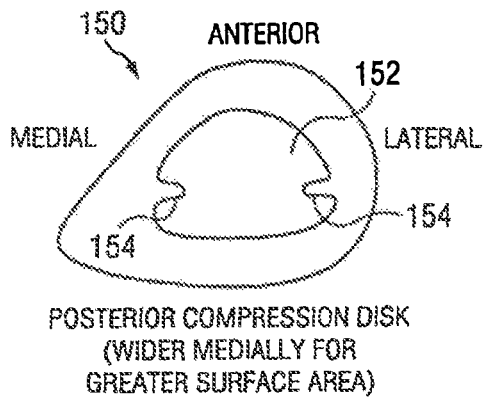
FIG. 4A is a top view of an embodiment of a compression disc used with embodiments of the intramedullary fixation device.

Nail 12 can be secured to outrigger assembly 20 as follows. The alignment between the proximal section 14 and distal section 16 in either the M-L or A-P orientation is determined by the surgeon and the notches 56 are mated with tab 38 for the desired alignment. To change alignment, the compression driver 24 facilitates the removal of the proximal section 14 from bolt 18 via socket 70. The proximal section 14, using notches 56 and tab 38, can be re-oriented and the compression driver 24 tightens the proximal section back on bolt 18 via socket 70. The notches 54 in the lower end 41 of distal section 16 of intramedullary fixation device or nail assembly 12 can be aligned in the desired position with tabs 130 on the outer end of shaft section 126 of nail mounting shaft 84. In addition, compression disc 150, shown in FIG. 4A, can be positioned between lower end 41 of nail 12 and tabs 130 so that it will be held between the lower end of the nail and forward end of shaft section 126. As shown in FIG. 4A, disc 150 has an aperture 152 through its center area, to accommodate shaft section 126 passing through such aperture. The purpose of disc 150 is to prevent the lower end of nail 12 from pulling upwardly into the calcaneus or heel bone when the bolt 18 is rotated to bring the distal section 16 of nail 12 upwardly to proximal section 14. Rather, with compression disc 150 abutting against the bottom surface of the patient's heel, the upward movement of distal section 16 will cause the spaces between the lower end of the tibia and top surface of the talus, as well as between the bottom surface of the talus and top surface of the calcaneus, to shrink and eventually be eliminated, as shown in FIGS. 2 and 3, and resulting in a desirably compressed ankle joint. In a preferred embodiment, the compression disc 150 is placed against the heel bone internal to the body. In an alternate embodiment, the compression disc 150 is placed against the heel bone external to the body.

Figure 17:
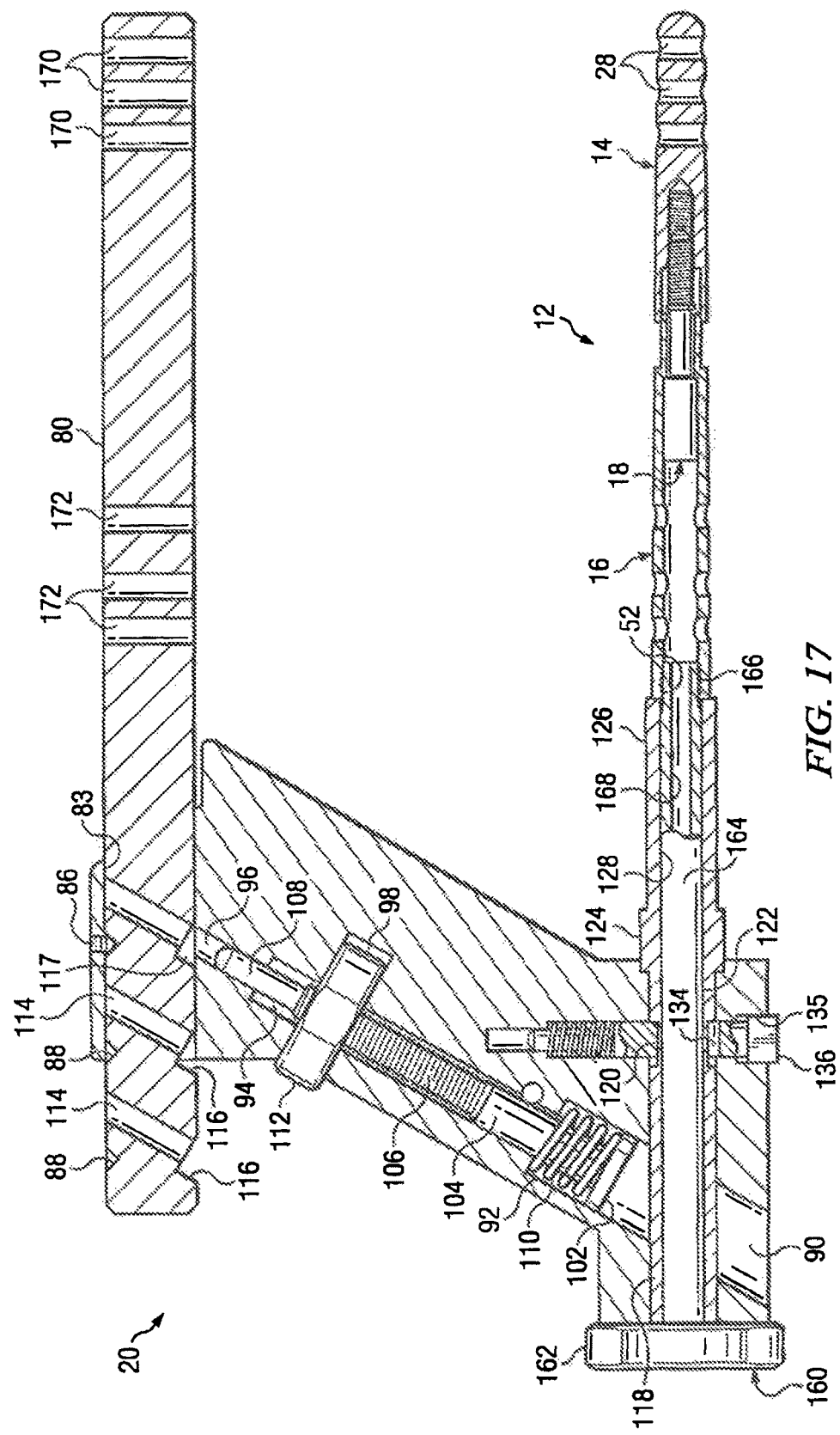
FIG. 17 is a cross-sectional view from the side of an embodiment of the outrigger assembly.

Once alignment tabs 130 on the outer end of shaft 84 have been engaged with notches 54 on the lower end 41 of nail 12, with compression disc 150 inserted in-between, then nail attachment device 160 can be used to secure nail 12 to shaft 84. As illustrated in FIG. 17, device 160 may comprise a knob 162 attached to one end of an elongated shaft 164 having male threads 166 on its opposite end. Shaft 164 is sized to be slidably received in cavity 128 in nail mounting shaft 84. In addition, a cavity 168 extends through shaft 164 from end to end. Male threads 166 can be engaged with female threads 52 on the lower end of distal section 16 of fixation device 12, thus causing nail 12 to be tightly secured to mounting shaft 84. Note also that compression bolt 18 can be pre-positioned in proximal and distal sections 14 and 16, so that the nail 12 is in an uncompressed state. After a hole has been is drilled upwardly through the bottom of the calcaneal bone C, talus A (if not so eroded or degraded that it no longer separates the tibia from the calcaneal bone) and into the medullary canal, the tibea T and cleaned out appropriately using techniques known to those skilled in the art, the forward end 25 of proximal section 14 of nail 12 can be inserted upwardly into such hole into the tibia, also in the known manner. Screw holes 170 are provided in the distal end of beam 80, which during use of outrigger assembly 20, can be aligned with holes 28 in proximal section 14 of nail 12. Similarly, similarly screw holes 172 in beam 80 can be aligned with holes 44 in distal section 16 of nail 12. Use of the outrigger assembly 20 with beam 80 assists the positioning and alignment of screws 30 with the tibia, talus, and calcaneus during insertion. Using outrigger assembly 20, holes can be then drilled into the tibia, which holes are aligned with holes 28 in nail 12, and been screws 30 can be inserted in such holes to secure proximal section 14 of nail 12 in position in the tibia. Then, compression driver 24 can be used rotate bolt 18, which movement causes distal section 16 to move upwardly towards proximal section 14. As shown in FIG. 16, compression driver 24 may include a handle section 180, a shaft or blade section 182 and a tip 184 which is designed to match and be received in socket 70 in the end of bolt 18. Blade section 182 is sized to slidingly fit through cavity 168 in nail attachment device 160, and is long enough so that tip 184 can be engaged with socket 70 in bolt 18. Bolt 18 can be turned so that threaded shaft section 64 is moved upwardly into threaded section 36 of proximal section 14 of nail 12, thus causing distal section 16 to slowly move upwardly toward proximal section 14. As indicated above and illustrated in FIGS. 3 and 4B, such movement causes the calcaneus and talus bones to also be forced to moved upwardly toward the lower end of the tibia. Eventually, by continuing to rotate driver 24 to turn bolt 18, an adequate amount of compression of the ankle joint can be accomplished, after which driver 24 may be removed from cavity 168 in mounting abaft 84. Then, the surgeon may secure the talus and calcaneus bones in such a compressed position against the lower end of the tibia by drilling the appropriate holes in the talus and calcaneus through apertures 172 in beam 80 of outrigger assembly 20, and the inserting screws through such holes and into holes 44 in distal section 16 of nail 12. Once properly secured, nail attachment device 160 can be removed from the lower end 41 of nail 12, and compression plate 150 can also be coincidentally removed. Preferably a suitable screw threaded cap can be placed over the lower end of nail 12 on threads 52.

Figure 4B:
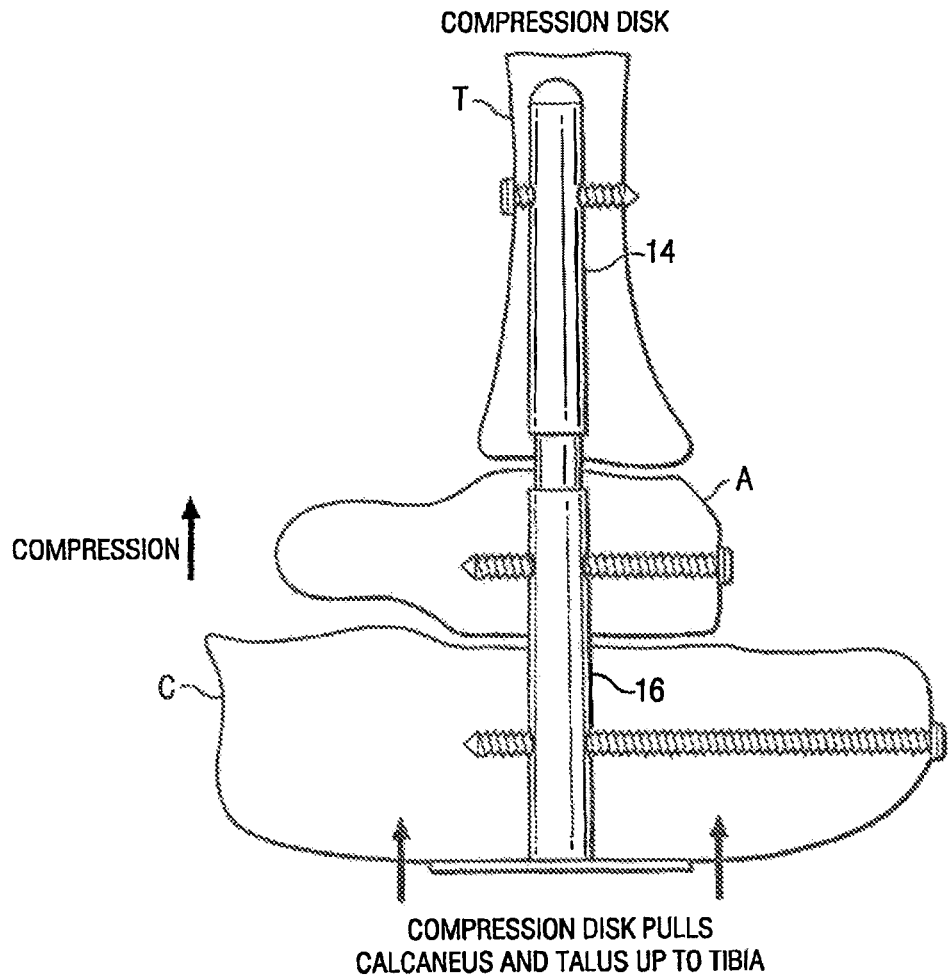
FIG. 4B is a side view of embodiments of the intramedullary fixation device and the compression disc as applied to an ankle joint in an uncompressed configuration.

FIGS. 2-3 are exemplary embodiments of uses for the intramedullary fixation device for use in ankle arthrodesis. FIG. 2 is a side view of the nail 12 in a non-compressed state in position within the tibia (T), talus (A) and calcaneus (C) bones. In FIG. 3 the nail 12 of FIG. 2 is in a compressed state. FIG. 4B is another view the nail of FIG. 2 in a non-compressed state along with the compression disc 150 being placed against the calcaneus hone. FIGS. 2 and 4 also show the direction of compression being applied.

FIGS. 18-20 are exemplary alternate embodiments of uses for the intramedullary fixation device. FIG. 18 is a side view of the intramedullary fixation device as applied to a fifth metatarsal fracture in an uncompressed configuration. The proximal portion 14 of nail 12 can be secured to a first portion of a metatarsal bone and the distal portion 16 of nail 12 can be secured to a second portion of the metatarsal bone. The direction of compression is also shown. A compression disc 150 can also be used and placed to provide a compressive force on the bones during compression of the nail 12 but prior to the distal portion 16 being affixed to the second portion of the metatarsal bone. The compression disc 150 may be placed internal or external to the body.

FIG. 19 is a side view of the intramedullary fixation device as applied to a long bone fracture in an uncompressed configuration. The proximal portion 14 of nail 12 is secured to a first portion of a long bone and the distal portion 16 of nail 12 is secured to a second portion of the long bone. The direction of compression is also shown. The long bone may be any bone having a fracture that would benefit from the compressive forces of nail 12 being applied thereupon. Examples of a long bone include the tibia and femur. A compression disc 150 can also be used and placed to provide a compressive force on the bones during compression of the nail 12 but prior to the distal portion 16 being affixed to the second portion of the long bone. The compression disc 150 may be placed internal or external to the body.

FIG. 20 is a side view of the intramedullary fixation device as applied to subtalar joint fusion in an uncompressed configuration. The proximal portion 14 of nail 12 is secured to the talus (A) and the distal portion 16 of nail 12 is secured to the calcaneus (C) bones. The direction of compression is also shown. A compression disc 150 can also be used and placed to provide a compressive force on the bones during compression of the nail 12 but prior to the distal portion 16 being affixed to the second portion of the calcaneus bone. The compression disc 150 may be placed internal or external to the body.

While many embodiments of the present invention have been described at some length and with some particularity with respect to the several described embodiments, it is not intended that it should be limited to any such particulars or embodiments or any particular embodiment, but it is to be construed with references to the appended claims so as to provide the broadest possible interpretation of such claims in view of the prior art and, therefore, to effectively encompass the intended scope of the invention.

I claim:

1. A method of stabilizing one or more bones with an intramedullary fixation device, the method comprising:
   providing an intramedullary fixation device comprising:
      a distal section having a reduced diameter arm on its upper end and an internal bore having a first section and a second section, the second section having a smaller diameter than the first section;
      a proximal section, the proximal section having an internal bore in its rearward end, the bore having a threaded area and a non threaded area, the non threaded area being sized to slidingly receive the reduced diameter arm;
      a connecting member for adjustably securing the distal and proximal sections end to end along a longitudinal axis, the forward end of the connecting member being threadably received in the threaded area of the proximal section internal bore, and the rearward end being sized to be received in the first section of the internal bore in the distal section;
      means for securing the proximal section to a first bone; and
      means for securing the distal section to a least one different bone, wherein the connecting member is rotated to provide compression across a bone arthrodesis site to be stabilized and fused;
   positioning the intramedullary fixation device with respect to the one or more bones;
   securing the proximal end of the intramedullary fixation device to a first bone location;
   securing the distal end of the intramedullary fixation device to a second bone location; and
   applying a compression force across the first and second bone locations.

2. The method of claim 1, wherein the first and second bone locations are on the same bone.

3. The method of claim 1, wherein the first and second bone locations are on different bones.

4. The method of claim 1, wherein the one or more bones is a long bone.

5. The method of claim 4, wherein the long bone is a femur.

6. The method of claim 4, wherein the long bone is a tibia.

7. The method of claim 4, wherein the long bone is a fibula.

8. The method of claim 4, wherein the long bone is a metatarsus.

* * * * *